United States Patent
Kirshner et al.

(10) Patent No.: US 11,124,756 B2
(45) Date of Patent: Sep. 21, 2021

(54) METHOD AND APPARATUS FOR ISOLATING INVASIVE AND METASTATIC CELLS FOR EVALUATING THERAPEUTICS AND PREDICTION OF METASTATIC CAPACITY

(71) Applicant: zPredicta, Inc., San Jose, CA (US)

(72) Inventors: Julia Kirshner, San Jose, CA (US); Mukti Rajen Parikh, San Jose, CA (US)

(73) Assignee: zPredicta, Inc., San Jose, CA (US)

( * ) Notice: Subject to any disclaimer, the term of this patent is extended or adjusted under 35 U.S.C. 154(b) by 51 days.

(21) Appl. No.: 16/216,097

(22) Filed: Dec. 11, 2018

(65) Prior Publication Data

US 2019/0284520 A1     Sep. 19, 2019

Related U.S. Application Data

(62) Division of application No. 15/112,408, filed as application No. PCT/US2015/012282 on Jan. 21, 2015, now Pat. No. 10,501,717.

(60) Provisional application No. 62/100,375, filed on Jan. 6, 2015, provisional application No. 61/930,390, filed on Jan. 22, 2014.

(51) Int. Cl.
| | |
|---|---|
| *C12M 1/34* | (2006.01) |
| *C12M 1/12* | (2006.01) |
| *C12M 1/42* | (2006.01) |
| *C12Q 1/04* | (2006.01) |
| *G01N 33/50* | (2006.01) |

(52) U.S. Cl.
CPC ............ *C12M 41/46* (2013.01); *C12M 25/04* (2013.01); *C12M 25/14* (2013.01); *C12M 35/08* (2013.01); *C12Q 1/04* (2013.01); *G01N 33/5011* (2013.01)

(58) Field of Classification Search
CPC ......... A61P 35/00; A61P 43/00; C12M 25/04; C12M 25/14; C12M 35/08; C12M 41/46; C12Q 1/04; G01N 33/5011
See application file for complete search history.

(56) References Cited

U.S. PATENT DOCUMENTS

| | | | |
|---|---|---|---|
| 4,829,000 | A | 5/1989 | Kleinman et al. |
| 7,544,465 | B2 | 6/2009 | Herlyn et al. |
| 2007/0160582 | A1 | 7/2007 | Madlambayan et al. |
| 2016/0178611 | A1 | 6/2016 | Han et al. |
| 2019/0169562 | A1 | 6/2019 | Kirshner et al. |

FOREIGN PATENT DOCUMENTS

| | | |
|---|---|---|
| WO | WO 2012/045368 | 4/2012 |
| WO | WO-2013040445 | 3/2013 |
| WO | WO-2013116729 | 8/2013 |
| WO | WO-2015112624 | 7/2015 |

OTHER PUBLICATIONS

International Search Report and Written Opinion of PCT/US2015/012282 dated Apr. 13, 2015 (10 pages).
Hulkower et al., "Cell Migration and Invasion Assays as Tools for Drug Discovery," Pharmaceutics, 2011, Vo. 3(1), p. 107-124, p. 107, para 1, p. 111, last para, and Fig. 2; p. 112, para 1; p. 116, para 2; amd p. 123, Ref. 50.
Ilkeda et al., "Inhibition by cardiac natriuretic peptides of rat vascular endothelial cell migation," Hypertension, 1995, vol. 26(3), p. 401-405, PDF File: 1-8, Abstract: p. 4, para 2 and Fig. 5; and p. 5, Selected Abbreviations and Acronyms.
Kurayoshi etal., "Expression of Writ-5a is Correlated with Aggressiveness of Gastic Cancer by Stimulating Cell Migration and Invasion," Cancer Res. 2006, vol. 66(21), p. 10439-10448, p. 10440, col. 1, para 1, and col. 2, para 2; and p. 10443, Fig. 2, Legend, and col. 2, top para.
Ma et al., "A porous 3D cell cultrure icro device for cell migation study," Biomed Microdevices, 2010, Vo. 12(4), p. 753-760, Abstract; p. 754, Fig. 1; and p. 755, col. 2, middle para, and Fig. 3.
Parikh et al., "A Reconstructed Metastasis Model to Recapitulate the Metastatic Spread in Vitro", NIH Public Access, Biotechnol J., Sep. 1, 2015 (pp. 1-22).
Sip et al., "Microfluidic Transwell Inserts for Generation of Tissue Culture-Friendly Gradients in Well Plates," 17th International Conference on Miniaturized Systems for Chemistry and Life Sciences, Freiburg, Germany, Oct. 27-31, 2013, Meeting Publication: p. 1436-1438, [online], http://www.rsc.org/images/loc/2013/PDFS/Papers/481_0459.pdf> Entire documentation, especially Abstract: p. 1436, Tehory; and p. 1437, Fig. 1(A), (C) and (D).
Albini et al., The chemoinvasion assay: a method to assess tumor and endothelial cell invasion and its modulation, Nature Protocols 2007, vol. 2, No. 3, pp. 504-511, XP055393578.
Anonymous: Transfilter Cell Invasion Assays, Biocyclopedia.com, Jan. 1, 2012, XP055393568, Retrieved from the Internet: biocyclopedia.com/index/cell_biology_methods/transfilter_cell_invasion_assays.php. Retrieved on Jul. 31, 2020. 10 pages.
Antonicelli et al., CXCL10 reduces melanoma proliferation and invasiveness in vitro and in vivo, British Journal of Dermatology 2011, 164, pp. 720-728.
Extended European Search Report for European Application No. 15740692.7 dated Aug. 3, 2017. 11 pages.
Gostner et al., Effects of EpCAM overexpression on human breast cancer cell lines, BMC Cancer 2011, vol. 11, article 45.

(Continued)

*Primary Examiner* — Blaine Lankford
(74) *Attorney, Agent, or Firm* — Sheppard Mullin Richter & Hampton LLP

(57) ABSTRACT

Embodiments provide methods to produce an assembly that mimics in vitro the human microenvironment of a primary tumor site, a secondary distant organ, and circulation. Methods and apparatuses that provide a platform for the isolation of primary tumor, invasive, and metastatic cells to be used for evaluation of therapeutic efficacy and diagnostics as applied to metastatic cancers are also provided.

20 Claims, 13 Drawing Sheets

(56) References Cited

OTHER PUBLICATIONS

Ha et al., Inhibitory effect of Sihoga-Yonggol-Moryo-Tang on matrix metalloproteinase-2 and -9 activities and invasiveness potential of hepatocellular carcinoma, Pharmacological Research 2004, vol. 50, No. 3, pp. 279-285, XP055393944.

International Preliminary Report on Patentability for International Application No. PCT/US2015/012282 dated Jul. 26, 2016. 7 pages.

FIG. 3B
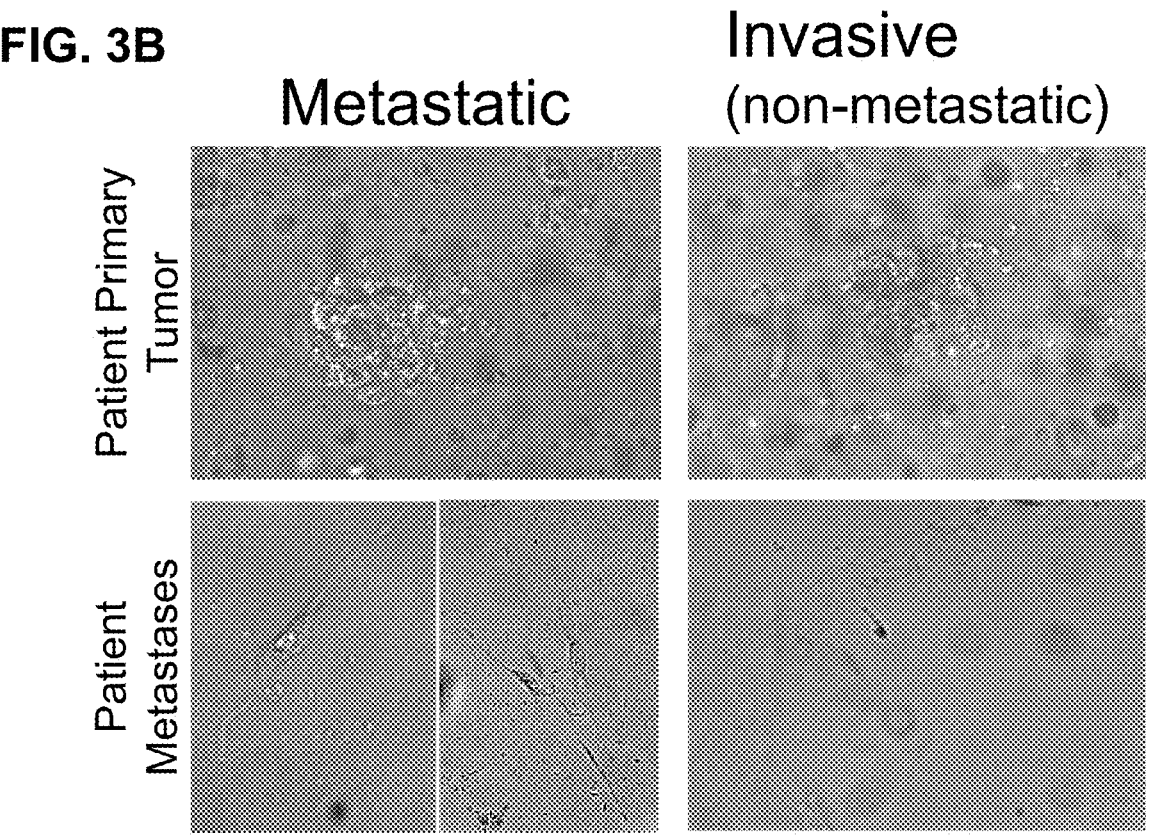
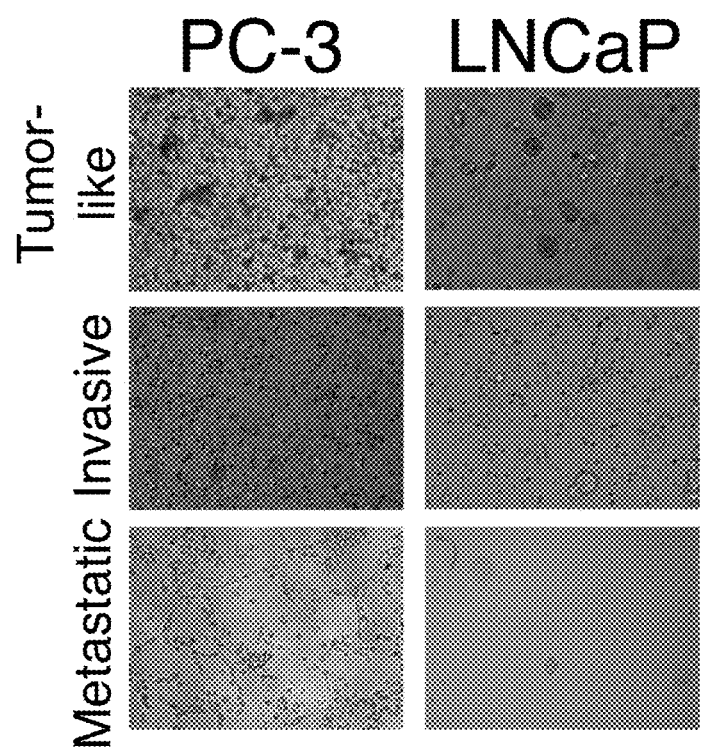
FIG. 3C

| MDA-MB-231 | MDA-MB-231-BO | MCF7 |
|---|---|---|
|  |  |  |
| PC-3 | LNCaP | A549 |
|  |  |  |

METHOD AND APPARATUS FOR ISOLATING INVASIVE AND METASTATIC CELLS FOR EVALUATING THERAPEUTICS AND PREDICTION OF METASTATIC CAPACITY

CROSS REFERENCE TO RELATED APPLICATIONS

This application is a divisional of U.S. patent application Ser. No. 15/112,408, filed Jul. 18, 2016, now U.S. Pat. No. 10,501,717, which is a U.S. National Stage Application under 35 U.S.C. § 371 of International Application No. PCT/US2015/012282, filed Jan. 21, 2015, which application claims the benefit under 35 U.S.C. § 119(e) of U.S. Provisional Application No. 61/930,390, filed Jan. 22, 2014 and 62/100,375, filed on Jan. 6, 2015, the contents of each of which are hereby incorporated by reference in their entireties.

TECHNICAL FIELD

Embodiments herein relate to a method and apparatus for culturing cells, and more specifically, to a method and apparatus for culturing cancer cells under the conditions that mimic the human microenvironment of a primary tumor site, a distant metastatic site, and circulation for investigation of cancer therapeutics and development of diagnostic and prognostic strategies for primary, in situ, invasive, metastatic, and recurrent cancers.

BACKGROUND

Metastasis is a complex multi-step process, whereby the malignant cells escape from the primary tumor, invade through the basement membrane of the tissue, survive in circulation under the conditions of anchorage-independence, and colonize the foreign microenvironment at a secondary site (Gupta G P, et. al., Cell, 127:679 (2006); Mehlen P, et. al., Nature Reviews Cancer, 6:449 (2006)).

Metastasis is responsible for significant morbidity associated with cancer and accounts for 90% of cancer-related deaths (Gupta G P, et. al., Cell, 127:679 (2006); Mehlen P, et. al., Nature Reviews Cancer, 6:449 (2006)). Despite the development of new treatment strategies, five-year survival rates for patients presenting with distant site metastases from most cancers remain below 30 percent (Society AC. Cancer Facts & Figures, American Cancer Society (2013)). The likely reason for such high mortality due to metastasis is the lack of effective therapeutic agents and early diagnostic strategies that identify and target specifically, the largely drug-resistant, metastatic cells.

To successfully colonize a secondary site, metastatic cells have to find a niche that will support their survival and growth. Such a niche is comprised of the extracellular matrix of a particular tissue, stromal, immune, and other cellular components, and secreted factors.

In vitro methods, such as the scratch assays, transwell migration assays, and invasion assays only evaluate the ability of cells to migrate on or through a solid substratum, and do not recapitulate the anchorage-independence required for metastatic dissemination through the circulation (Kam Y, at. al., BMC Cancer, 8:198 (2008); Kramer N, et. al., Mutation Research/Reviews in Mutation Research (2012); Liang C-C, et. al., Nature Protocols. 2:329 (2007)). Furthermore, the invasion assays, such as Matrigel invasion, fail to account for the differences in the extracellular matrix composition of the primary and secondary sites (Ioachim E, et. al., European Journal of Cancer, 38:2362 (2002)). These shortcomings largely limit the use of the standard in vitro methods to the studies of either dissemination of tumor cells from the primary site or invasion of the secondary organ, but not both. Mouse models of metastasis are equally inadequate for pre-clinical use because they do not faithfully recapitulate human disease.

SUMMARY

The present disclosure is directed to a cell culture assembly, a comprehensive system that mimics in vitro the human microenvironment of a primary tumor site, a secondary distant organ, and circulation. The cell culture assembly is sometimes referred to herein as a reconstructed metastasis model or "rMet" system, culture, platform, or model. The data provided herein shows that the rMet system recapitulates all stages of tumorigenesis (i.e. primary tumors, invasive, metastatic and recurrent cancers) and the major steps of the metastatic spread: 1) escape from the primary site, 2) invasion through the basement membrane, 3) survival under conditions of anchorage-independence, and 4) invasion/colonization of a secondary site. Furthermore, the rMet system is designed to take into account the extracellular matrix of both the primary and secondary sites, thus overcoming the major limitations of the currently used systems.

In one embodiment is provided a cell culture assembly comprising: a) a first component comprising a fluid derived from a vertebrate and optionally a primary site growth matrix, b) a second component comprising a biological matrix mimetic, and c) a dynamic fluid component comprising a secondary site growth medium, synthetic or derived from a vertebrate, wherein the fluid component is in fluid contact with the first and second component. In some embodiments, the secondary site growth medium has a higher serum concentration than the fluid. For instance, the secondary site growth medium can have a serum (or substitute serum or replacement serum) concentration in the range of 10-30%, while the fluid has a serum concentration between 0% and 5%.

In another embodiment is provided a method of identifying an anticancer therapeutic comprising: a) adding a solution comprising a potential anticancer therapeutic to the cell culture assembly as described herein, wherein the second component of the cell culture assembly comprises a detectable amount of cancer cells, including, but not limited to primary tumor cells, invasive cells, and/or metastatic cells, b) detecting the amount of primary tumor cells, invasive cells, and/or metastatic cells present in the cell culture assembly before and after the addition of the potential anticancer therapeutic, and c) identifying a potential anticancer therapeutic.

In another embodiment is provided a method of identifying the efficacy of an anticancer therapeutic on a patient comprising: a) adding a solution comprising a potential anticancer therapeutic to the first component of the cell culture assembly as described herein, wherein the second component of the cell culture assembly contains a detectable amount of cancer cells, including, but not limited to primary tumor cells, invasive cells, and/or metastatic cells, b) detecting the amount of primary tumor cells, invasive cells, and/or metastatic cells present in the second component before and after the addition of the potential anticancer therapeutic, and c) identifying the efficacy of an anticancer therapeutic.

In another embodiment is provided a method of predicting and/or identifying metastatic dissemination of a cancer in a patient comprising: a) adding a solution comprising cancer cells obtained from the patient to the first component of cell culture assembly as described herein, wherein the second component of the cell culture assembly comprises a detectable amount of cancer cells from the patient, and b) detecting the presence or absence of metastatic cancer cells in the second component of the cell culture assembly after a sufficient period of time.

Further embodiments may be found throughout the description.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIG. 1A is showing an assembly of the rMet model as a cell culture apparatus mimicking a primary site (insert) and a secondary site (a well of a tissue culture plate) in vitro (reconstructed metastasis, rMet model) with an optional device agitating the fluid in the assembly; FIG. 1B illustrates cryo-scanning electron microscopy images of solidified Matrigel ("primary site" extracellular matrix); FIG. 1C illustrates cryo-scanning electron microscopy images of polymerized reconstructed bone marrow (rBM) matrix; and FIG. 1D illustrates cell distribution after a period of time in rMet culture.

FIGS. 3A-D show that the rMet model recapitulates the complexity of solid tumor metastasis; FIG. 3A shows the formation of a tumor-like, invasive, and metastatic cell populations by the breast cancer cells cultured in rMet; FIG. 3B shows the formation of a tumor-like and metastatic cell populations by the primary breast cancer cells cultured in rMet; FIG. 3C shows the formation of a tumor-like, invasive, and metastatic cell populations by the prostate cancer cells cultured in rMet; FIG. 3D shows the formation of a tumor-like, invasive, and metastatic cell populations by the lung, stomach, pancreas, colon, ovarian, melanoma, and testicular cancer cells cultured in rMet.

FIG. 7A illustrates that metastatic cells isolated from the rMet model induce metastasis while tumor-like cells have a severely diminished capacity to spread in vivo. FIG. 7B illustrates an appearance of metastatic lesions at various secondary sites.

DETAILED DESCRIPTION

Figure 1A:
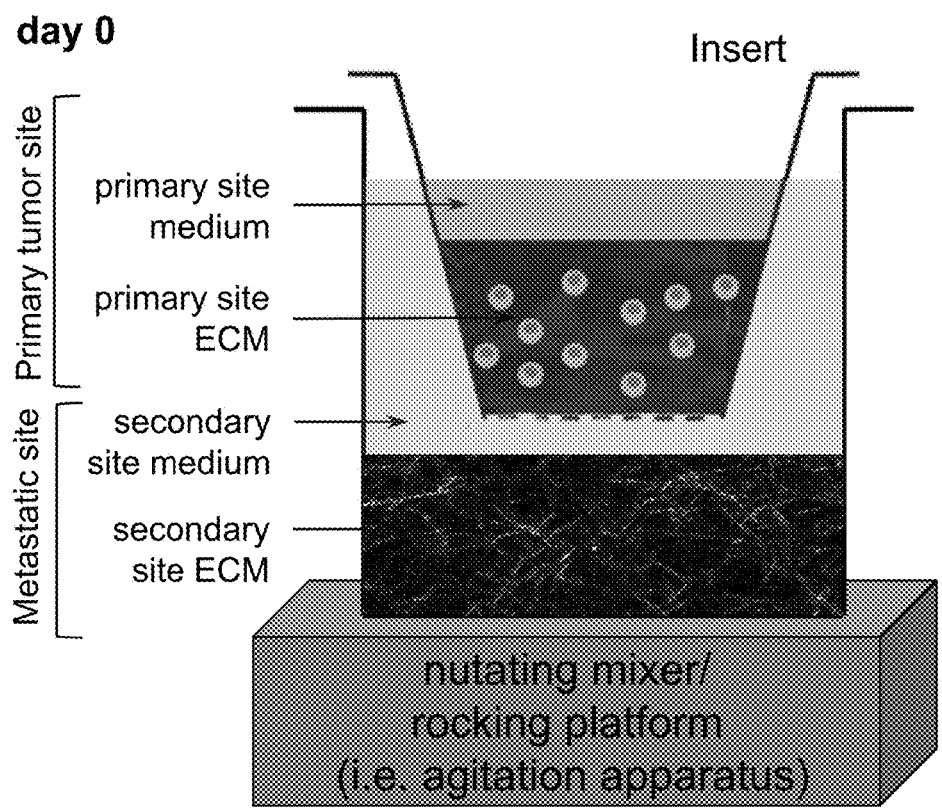
FIGS. 1A-D illustrate the assembly of the rMet model designed to mimic an in vivo microenvironment of a primary tissue and a secondary organ, in accordance with various embodiments.

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, over/under, back/front, and top/bottom. Such descriptions are merely used to facilitate the discussion and are not intended to restrict the application of embodiments.

Definitions

Provided herein is a cell culture assembly that cultures eukaryotic cells in vitro in an apparatus designed to reconstruct the process of cell migration from a primary site in an organism to a secondary location. As mentioned above, the cell culture assembly which is a reconstructed metastasis model is sometimes referred to as the "rMet" model or system or cell culture apparatus or platform. The rMet model allows tumor cells to disseminate from a primary tissue site, for example, the mammary gland, to a secondary site, for example, the bone marrow in a manner that more closely resembles their spread in vivo than is possible using traditional culture methods. The rMet model offers an improved opportunity for isolating primary tumor, invasive, and metastatic cells to be used for therapeutic development, anticancer drug testing, evaluation of response to treatment, and prediction of metastatic capacity of individual tumors.

Terms used to describe the rMet model are provided below.

The cell culture assembly may employ tissue culture vessels or cell culture vessels. For the purposes of describing embodiments, the phrases "tissue culture vessel" and "cell culture vessel" are interchangeable and refer to any vessel/ container suitable for the growth of eukaryotic cells, including any vessels/containers commercially available or custom-made for that purpose. In some embodiments, the phrases "tissue culture insert", "cell culture insert", "insert vessel", or "transwell" refer to an apparatus designed to be placed into a tissue culture vessel for a purpose of creating multiple segregated chambers. Tissue culture vessels or vessel inserts may be constructed from materials including, but not limited to, polystyrene, a polymer, glass, plastic, etc. and may be treated/coated/constructed with a surface adapted for cell attachment. Inserts may have a porous membrane constructed from such materials as polyethylene terephthalate, polycarbonate, or any other suitable material. Surfaces of tissues culture vessels and/or inserts may be hydrophilic, hydrophobic, negatively charged, positively charged, non-ionic, or altered in texture to increase one or more surface areas. In addition, tissue culture vessels may be gas permeable and/or may include a cap/lid/closure that is gas permeable. Tissue culture vessels in accordance with embodiments include, but are not limited to, flasks, single well plates, multi-well plates, microtiter plates, bottles, Petri dishes, chamber slides, and other containers.

As used herein the term "fluid derived from a vertebrate" may include, but is not limited to, plasma, or serum from blood or bone marrow, peritoneal fluid, ascites fluid, cerebrospinal fluid, whole blood, lymph and/or synovial fluid, tears, urine, saliva or any other gastrointestinal fluids from any vertebrate animal (including but not limited to humans, non-human primates, rats, mice, rabbits, pigs, dogs, and others). The vertebrate may be healthy, may have cancer or a premalignant syndrome. In one embodiment where the vertebrate does not have cancer and is healthy, tumor cells from the same source or different source may be added to the system. In embodiment where the vertebrate has cancer, this fluid may include plasma, serum, peritoneal fluid, ascites fluid, cerebrospinal fluid, blood, lymph and/or synovial fluid from any vertebrate animal (including but not limited to humans, non-human primates, rats, mice, rabbits, pigs, dogs, and others) with any form of cancer, including but not limited to solid tumors, cancers of bone, soft tissue, muscle, skin and/or blood. For the purposes of describing embodiments, the phrases "healthy vertebrate", "normal vertebrate", or "disease-free vertebrate" are used interchangeably and describe a vertebrate animal that is free of any disease condition or pathology.

In some embodiments, the first component may also include a "primary site growth matrix" which is intended to mimic the primary tumor growth site or a healthy tissue, such as an organ. The primary tumor site may be selected from a variety of sites, including bladder, bone, brain, breast, cervix, colon, esophagus, kidney, liver, lung, skin, ovary, pancreas, prostate, stomach, uterus, testicles, thyroid, and the like. In some embodiments, this matrix comprises a cell culture medium comprising RPMI-1640 with L-glutamine (or other growth medium) and about 1% horse serum. The matrix may also include an antimicrobial, antibiotic, and/or antifungal substance. For example, in some embodiments illustrated herein, growth medium comprises RPMI-1640 with L-glutamine, 20% fetal bovine serum (FBS), $6.2 \times 10^{-4}$M $CaCl_2$, $1 \times 10^{-6}$M sodium succinate, and $1 \times 10^{-6}$M hydrocortisone and 1% penicillin/streptomycin.

Additional components for the primary site growth matrix may be selected based on the primary tumor site. Additional components may include basement membrane (BM), collagen (defined below as CI-V for collagen I, collagen II, collagen III, collagen IV, collagen V), fibronectin (FN), laminin (LN), hyaluronic acid (HA), elastin, lecticans, and the like.

Exemplary primary site growth matrices are presented in Table IA below. Also provided are representative concentrations and ranges of appropriate concentrations.

TABLE IA

Primary Site Growth Matrix

| Primary Tumor Site - Organ | Matrix | Matrix concentration | Concentration range |
|---|---|---|---|
| Bladder | LN; FN; CI; CIII; elastin | 1:2:4:1:1 | (1-2):(1-2):(2-6):(0-1):(0-1) |
| Brain | HA; lecticans | 5:1 | (2-10):1 |
| Breast | Matrigel[#] | 1 | n/a |
| Cervical | HA; CI; CIII | 5:1:1 | (2-10):(1-5):(0-1) |
| Colon | Matrigel; FN | 2:1 | (2-4):(1-3) |
| Esophagus | LN; FN; CI; CIII; elastin | 1:2:4:1:1 | (1-2):(1-2):(2-6):(0-1):(0-1) |
| Kidney | FN; CI; CIII | 2:3:1 | (1-2):(1-5):(0-1) |
| Liver | Matrigel; FN; HA (BM) | 4:2.5:1 | (2-6):(2-3):(1-3) |
|  | CI; CIII; CV | 5:1:1 | (5-10):1:1 |
| Lung | Matrigel (BM) | 1 | n/a |
|  | Matrigel; FN | 2:1 | (2-4):(1-3) |
| Melanoma | Matrigel | 1 | n/a |
| Ovarian | LN; FN; HA; CI; CIII | 1:2:3:2:1 | (1-2):(1-2):(1-4):(1-4):(0-1) |
| Pancreas | Collagen I | 1 | n/a |
| Prostate | Matrigel | 1 | n/a |
| Sarcoma | Matrigel; FN; HA; CI[1]/CI[2]/CIII[3] | 4:2:2:2 | (3-6):(1-3):(1-4):(1-2) |
| Stomach | Matrigel; FN; HA | 4:2.5:1 | (2-6):(2-3):(1-3) |
| Testicular | Matrigel | 1 | n/a |
| Thyroid | Matrigel; FN | 2:1 | (2-4):(1-3) |

[#]Matrigel:
LN; CIV (major components)
[1]osteosarcoma;
[2]myosarcoma;
[3]chondrosarcoma For the purposes of describing embodiments, the phrases "biological matrix mimetic," "reconstructed organ matrix", "organ-specific matrix", or "extracellular matrix" refer to any substance, solution, mixture, including a commercially available product such as Matrigel®, that is designed, produced, or used to mimic or approximate in vitro one or more biological matrices such as, for example, an extracellular matrix, an intracellular matrix, a basement membrane, and/or a structure of a connective tissue. This matrix mimics the site of the metastasis or secondary site. Matrices may be selected based on the secondary site or metastatic site. Additional components may include basement membrane (BM), collagen (defined below as CI-V for collagen I, collagen II, collagen III, collagen IV, collagen V), fibronectin (FN), laminin (LN), hyaluronic acid (HA) or related hyaluronans, elastin, lecticans, Matrigel® or other glycosaminoglycans, chondroitins, dermatans, or related extracellular matrix or glycocalyx components or combinations thereof, and the like. Representative matrices and concentrations are shown below in Table IB.

TABLE IB

Biological Matrix Mimetic

| Organ | Matrix | Matrix concentration | Concentration range |
|---|---|---|---|
| Adrenal gland | Matrigel; FN; CI | 4:2.5:1 | (3-6):(2-4):1 |
| Bone | FN, CI (endosteum) | 1:1 | (7.5-3.5):1 |
|  | Matrigel; FN; CI, HA | 4:2.5:1:1 | (3-6):(2-3):1:1 |
| Brain | HA; lecticans | 5:1 | (2-10):1 |
| Liver | Matrigel; FN; HA | 4:2.5:1 | (2-6):(2-3):(1-3) |
|  | (BM) CI; CIII; CV | 5:1:1 | (5-10):1:1 |
| Lung | Matrigel (BM) | 1 | n/a |
|  | Matrigel; FN | 2:1 | (2-4):(1-3) |
| Lymph node | Matrigel; FN; CI; CIII | 4:2.5:1:1 | (3-6):(2-4):(1-5):(0-1) |
| Ovary | Matrigel | 1 | n/a |
| Peritoneum | Matrigel; CI; FN | 4:2.5:1 | (3-6):(2-4):1 |
| Skin | Matrigel; FN | 2:1 | (2-4):(1-3) |
|  | (BM) CI; CIII | 3:1 | (1-6):(0:3) |
| Spleen | Matrigel; HA | 4:1 | (2-6):(1-10) |
|  | (BM) FN; CI | 2:1 | (2-4):1 |

For the purposes of describing embodiments, the phrase "secondary site growth medium" refers to a cell culture medium comprising RPMI-1640 with L-glutamine or a suitable growth medium, fluid from a culture of bone marrow stromal cells, or a fluid from a vertebrate supplemented with $6.2 \times 10^{-4}$M $CaCl_2$, $1 \times 10^{-6}$M sodium succinate, and $1 \times 10^{-6}$M hydrocortisone. Growth medium may also include an antimicrobial/antibiotic/antifungal substance. Horse serum or fluid from a culture of bone marrow stromal cells may be substituted for a fluid from a healthy vertebrate or a vertebrate with cancer. The molarity and/or molality of each component in growth medium may vary among embodiments. "Fluid from a culture of bone marrow stromal cells" may include cell culture medium collected from the cultures of bone marrow stromal cells that may include, but not limited to, bone marrow stromal cell lines or primary bone marrow cells from any vertebrate animal (including but not limited to humans, non-human primates, rats, mice, rabbits, pigs, dogs, and others). The phrase "culture of bone marrow stromal cells" refers to a system where primary bone marrow cells or bone marrow cell lines are grown in a tissue culture vessel overlaid with cell culture medium.

It is contemplated that the fluid and optionally the primary site growth matrix simulate the primary tumor site where a tumor cell is originated. During metastasis, a primary tumor cell needs to invade and migrate to a different site, which biological matrix mimetic at the second component of the present technology simulates. The invasion and migration in vivo is mediated by the circulation system. In the present technology, the dynamic fluid component simulates the circulation system and the secondary site growth medium inside simulates circulating blood or lymph.

In this context, it is hereby discovered that the simulation efficiency of the present system is enhanced when the secondary site growth medium contains higher serum content than the fluid. For instance, the secondary site growth medium can have a serum concentration in the range of 8%-35%, or more particularly 10%-30%. By contrast, the serum content in the fluid of the first component can be from 1% to 5%, or more generally 0.5% to 6%.

As well known in the art, serum is the blood component after blood cells and clotting factors are removed and is the blood plasma not including the fibrinogens. Serum includes all proteins not used in blood clotting and all the electrolytes, antibodies, antigens, hormones, and any exogenous substances. Natural serum can be isolated from blood of vertebrates, either healthy or having cancer.

Synthetic, substitute or replacement serum (collectively referred to as "substitute serum") can also be made and is commercially available. Substitute serums typically include most or all major serum proteins found in vertebrates. The major serum proteins include, for instance, albumins, globulins, and regulatory proteins. More specific examples include, without limitation, prealbumin, alpha 1 antitrypsin, alpha 1 acid glycoprotein, alpha 1 fetoprotein, alpha2-macroglobulin, gamma globulins, beta-2-microglobulin, haptoglobin, ceruloplasmin, Complement component 3, Complement component 4, C-reactive protein (CRP), lipoproteins (chylomicrons, VLDL, LDL, HDL), transferrin, Mannan-binding lectin, and mannose-binding protein.

In some aspects, the serum or substitute serum concentration in the secondary site growth medium is at least 8%, 9% 10%, 12%, 15%, 18%, 20% or 25%. In some aspects, the serum or substitute serum concentration in the fluid of the first component is less than 6%, 5.5%, 5%, 4.5%, 4%, 3%, 2%, or 1.5%. In some aspects, the serum or substitute serum concentration in the secondary site growth medium is at least 50% higher than, 80% higher than, or is two times, three times, four times or five times the serum or substitute serum concentration in the fluid of the first component.

Additional components may be coupled, e.g., an incubator, microscope, pump, etc., to the cell culture assembly. The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of describing embodiments, the phrase "incubator" is a temperature controlled, humidified chamber with controlled carbon dioxide ($CO_2$) environment for maintaining cell cultures at temperatures between 30-45° C. and 1-10% $CO_2$.

As used herein, the phrases "solid tumor" refers to any cancer of non-hematopoietic origin and "anticancer therapeutic" refers to any compound, chemical, substance or a combination of such compounds, chemicals, substances, nanoparticles, or other drug delivery vehicles that prevent the growth or migration of cancer cells, induce cell death in cancer cells, and/or are detrimental to the survival and expansion of a cancer cell population.

For the purpose of describing the embodiments, the phrases "tumor", "cancer", "malignancy", and "neoplasm" are used interchangeably.

Cell Culture Assembly and its Components

Provided herein is a unique system that provides a platform for separation of tumor cell populations to isolate cells at different stages of tumorigenesis (such as primary tumor, invasive, and metastatic cells, as well as the cells from recurring/relapsing cancers.

Greater than 90% of anticancer drugs do not reach the market because they fail during clinical development. Despite demonstrating high efficacy in animal models during pre-clinical development, the highest rates of attrition of new therapeutics are seen in phases II and III clinical trials, the efficacy phases. This suggests that the in vivo rodent models of experimental metastasis used for preclinical development do not faithfully recapitulate the microenvironment of the human tissues. Thus, a comprehensive 3-dimensional (3-D) in vitro reconstructed metastasis (rMet) model was developed where the distinct tissue-specific human microenvironments of the primary and the secondary sites are incorporated into a single assay to recapitulate the major phases of metastasis (escape from the primary site and colonization of a distant organ), including the anchorage-independent step. The modular design of the rMet system allows for the organ-specific microenvironment to be set-up, reconstructing the primary and secondary sites, as well as the circulatory environment of the human tissue. The presence of specific extracellular matrix components enables successful expansion of human tumor and non-malignant cells and preserves the cell-cell interactions similar to those in vivo.

Not only does the rMet model allow isolation of metastatic and invasive cell populations, it provides a comprehensive system to study the basic biology of cancer and its spread. The rMet model is a useful tool to design and evaluate novel therapeutics targeting the primary tumor, invasive and metastatic populations, to personalize treatment regimens to identify drugs that will be efficacious for individual patients, and to predict the metastatic capacity of individual tumors. These embodiments are more thoroughly described below. Moreover, this model is adaptable for high-throughput analysis of drugs with potential to target specific cellular compartments.

A variety of primary tumor sites and metastatic tumor sites may be investigated using the methods and systems described herein. For example, primary tumor sites include, but are not limited to, bladder, bone, bone marrow, brain, breast, cervix, colon, endometrium, esophagus, intestine, kidney, liver, lung, mouth, muscle, ovary, skin, pancreas, prostate, skin, stomach, testicles, thyroid, uterus, as well as any hyperproliferative tissues, including vascular structures (e.g., endothelial cells, smooth muscle cells, pericytes, scars, fibrotic tissue, surgical adhesion tissue or hyperproliferative bone lesions) and the like.

A variety of metastatic sites may also be investigated using systems described herein. These sites include, but are not limited to, adrenal gland, bone, brain, kidney, liver, lung, lymph node, ovary, peritoneum, skin, spleen, and the like. In one embodiment, the cell culture assembly does not include the combination of a primary site of mammary gland and the metastatic site of bone marrow.

In one embodiment, the cell culture assembly comprises a fluid derived from a vertebrate and optionally a primary site growth matrix, a second component comprising a biological matrix mimetic, and a dynamic fluid component comprising a secondary site growth medium wherein the fluid component is in fluid contact with the first and second component.

A variety of cells may be cultured in the cell assembly described herein. In certain embodiments, cells cultured may include epithelial cells, hematopoietic cells, stromal cells, and/or any other eukaryotic cells. While some embodiments are directed to culturing cancer cells, also encompassed by this disclosure are assemblies, apparatuses and methods for culturing any cell type, including but not limited to blasts, polymorphonuclear cells, neutrophils, eosinophils, basophils, pre-PMN cells, promyelocytes, myelocytes, metamyelocytes, lymphocytes, B and/or T cells, nucleated red cells, proerythroblasts, basophilic erythroblasts, polychromatophilic erythroblasts, orthochromatic erythroblasts, macrophages, fibroblasts, myoepithelial cells, mesenchymal stem cells, reticular cells, osteoclastic cells, osteoblastic cells, chondrocytes, epithelial cells, mesenchymal cells, neuronal cells, etc.

In an embodiment, the first component comprises a fluid derived from a vertebrate. In some embodiments, the fluid is from a vertebrate with cancer. This component may mimic the primary tumor site. Some embodiments further comprise adding a fluid derived from a healthy vertebrate or a vertebrate with cancer onto the surface of the biological matrix mimetic, while other embodiments further comprise adding a cell culture fluid and/or diluent onto the surface of the biological matrix mimetic. Some embodiments include fluid with hematopoietic or stromal components from a vertebrate. One or more cell adhesion factors, or other factors, including, but not limited to, hormones, growth factors, cytokines, chemokines, may also be added to the biological matrix mimetic and/or to a fluid.

The second component comprises a biological matrix mimetic. This component mimics the metastatic site. In one embodiment, the matrix mimetic is organ specific. In one embodiment, the organ specific-matrix simulates the adrenal gland, bone marrow, brain, liver or lung tissue, lymph node, ovary, peritoneum, skin, spleen, connective tissue, bone, vascular structure, or articular joint, or the like.

While Matrigel® is the biological matrix mimetic in some embodiments, in other embodiments another biological matrix mimetic and/or one or more components of Matrigel® may be substituted as the biological matrix mimetic.

As eluded to above, both the primary site growth matrix, the secondary site medium, and the biological matrix mimetic may comprise cell adhesion factors. Cell adhesion factors are well known in the art and include fibronectin, collagen I, collagen II, collagen III, collagen IV, collagen V, laminin, elastin, vitronectin, tenascin, hyaluronic acid, lecticans, positively-charged molecules ((such as poly-1-lysine, chitosan, poly(ethyleneimine), polymerized acrylics, etc.)), cell surface carbohydrate-binding proteins/glycoproteins, integrins, cadherins, fragments/subunits of cell adhesion molecules, synthetic analogs of cell adhesion molecules, gelatin, poly-1-ornithine, etc. Embodiments may include 1, 2, 3, 4, 5, 6, or more of these factors as components of each mixture, and/or include one or more as additives to a fluid derived from a healthy vertebrate or a vertebrate with cancer. In addition, the ratios and/or concentrations of these factors may vary among embodiments.

Additionally, one or more diluents and/or cell culture media may be added to any of the mixtures and/or to the fluid from a vertebrate. Diluents/media may include water, phosphate-buffered saline (PBS), RPMI-1640 growth medium, Minimal Essential Medium (MEM), Eagle's Basal Medium (BME), Dulbecco's Modified Eagle's Medium (DMEM), Hank's Balanced Salt Solution (HBSS), and their modifications, etc. Cell culture media may be fresh or collected from a culture of vertebrate cells.

The first and second components are in fluid contact with a static or dynamic fluid component. The dynamic fluid component mimics the circulatory system. This component comprises the secondary site growth medium as described throughout. The fluid may be made dynamic by agitating or stirring the assembly. Optionally, the assembly may be coupled to a mechanical device that would move the system. In one embodiment, the assembly may be coupled or connected to a stirring device or even a pump. This is more thoroughly discussed below.

The first and second components are in fluid contact with the static or dynamic fluid layer. In one embodiment, the first component and the second component comprise a membrane or other porous component allowing the component's contents to move from the first component through the dynamic fluid component and to the second component.

Methods of Making and Using the Cell Culture Assembly

Figure 2:
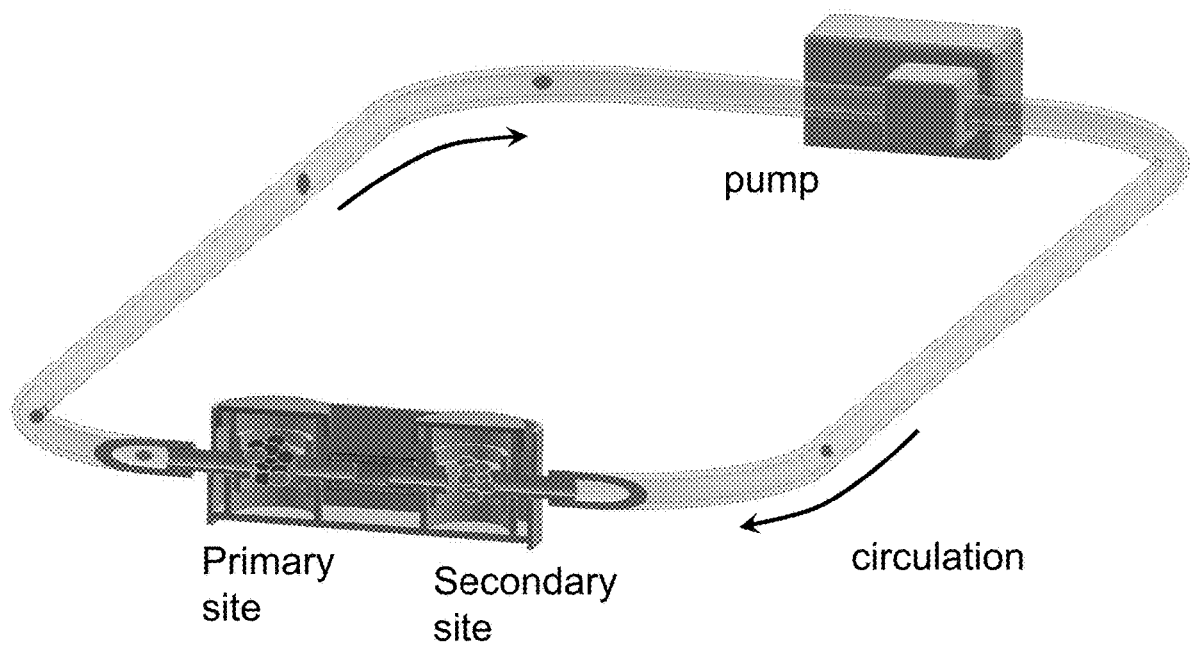
FIG. 2 illustrates an alternative assembly of the rMet model where a primary tissue and/or a secondary site are set-up in separate vessels connected by a source moving the fluid between the vessels.

The cell culture assembly may be vertical, as shown in FIG. 1A, or may be horizontal, as shown in FIG. 2.

FIG. 1A is a schematic illustration demonstrating the basic components and the assembly of the rMet model. In this embodiment, Matrigel was combined with human cancer cells and the mixture was added to a cell culture insert with 8 μm pores, which was then inserted into a well of a tissue culture plate containing the rBM matrix. It is contemplated that suitable pore size could be readily determined by one of skill in the art. Representative inserts have a pore size of from about 4 μm to about 10 μm. To complete a primary tumor site set up in the cell culture insert, the cell/Matrigel mixture was overlaid with growth medium. To assemble the microenvironment of the metastatic site bone marrow culture medium (BMCM) was added to the rBM-containing tissue culture well. The entire assembly was placed on a nutating mixer to agitate the media over the matrix. This nutating mixture is just one option for providing the movement of the fluid component. While this drawing refers to bone marrow culture medium, a variety of mediums can be employed, including, but not limited to growth medium, fluid from a healthy vertebrate or a vertebrate with cancer, etc.

Figure 1B:
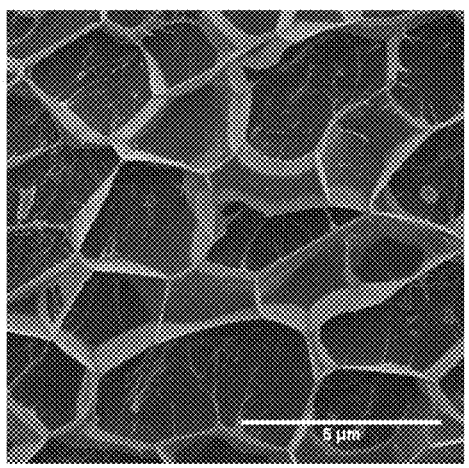
Figure 1C:
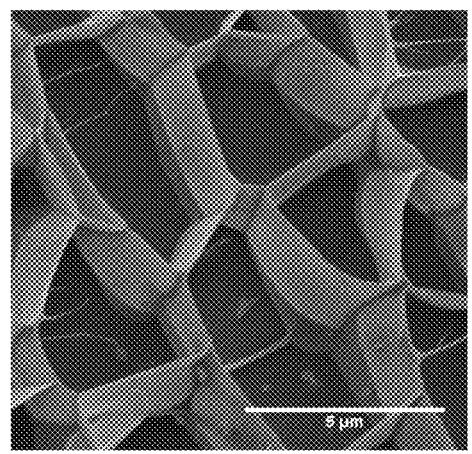
Figure 1D:
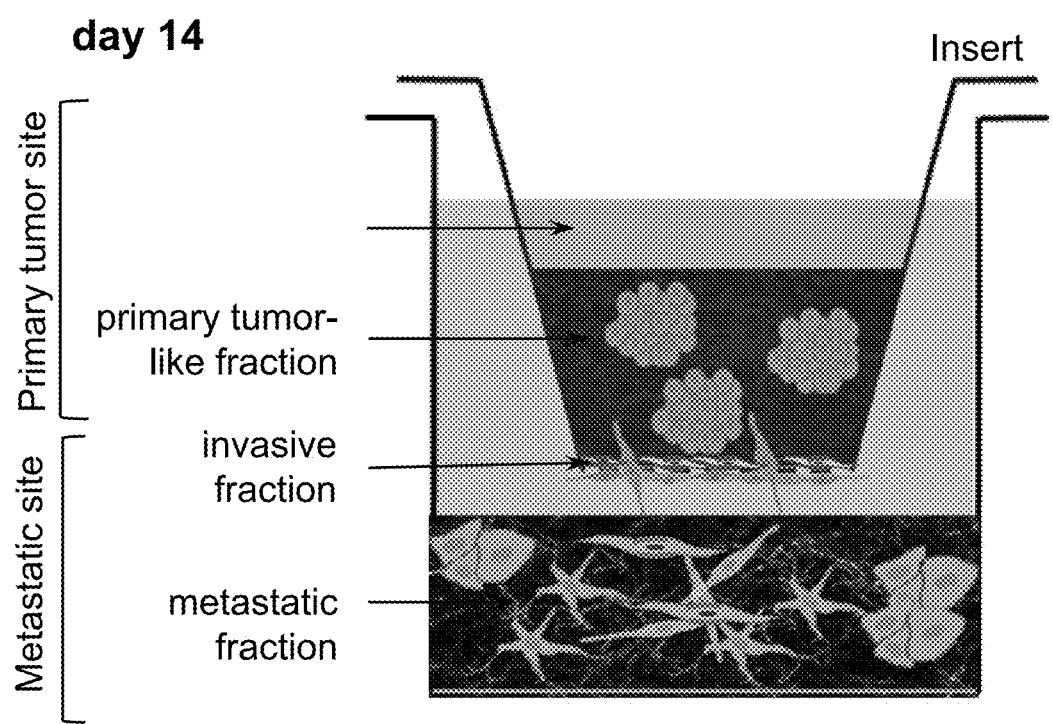

FIG. 1B illustrates the structure of polymerized Matrigel visualized by cryo-scanning electron microscopy (scale bar: 5 μm). FIG. 1C illustrates the structure of polymerized rBM visualized by cryo-scanning electron microscopy (scale bar: 5 μm). FIG. 1D illustrates the distribution of cells after 14 days in rMet culture into a tumor-like fraction consisting of spheroids trapped within the Matrigel of the insert. The invasive fraction comprised of cells that invaded through the Matrigel and formed a monolayer on the membrane surfaces of the insert. Finally, the metastatic population invaded through the Matrigel, survived in the BMCM under the conditions of anchorage-independence, and colonized the rBM matrix.

In some embodiments, the rMet model incorporates organ-specific extracellular matrix components to study solid tumor metastasis in a physiologically relevant manner. In certain embodiments, the rMet model includes a tissue culture insert incorporating a biological matrix mimetic forming a gel with cell culture medium overlay that is subsequently inserted into a tissue culture vessel coated with a first mixture, a second mixture including a biological matrix mimetic forming a gel over the first mixture, and a cell culture medium overlaying the second mixture. In some embodiments, human cancer cells are embedded in gel inside an insert designed to reconstruct the primary site. The insert is subsequently placed inside a tissue culture vessel where the gel and medium have been set-up. Methods of forming the rMet cell cultures according to embodiments are further described herein.

In some embodiments, a method for forming the rMet model includes placement of a biological matrix mimetic into a tissue culture insert with a porous membrane to mimic the primary tumor site and overlaying the mixture with cell culture medium and inserting the insert into a tissue culture vessel coated with a biological matrix mimetic to mimic the basement membrane of the tissue of interest, overlaid with a mixture that forms a gel to mimic the tissue, overlaid with cell culture media. An agitation apparatus, selected from a peristaltic or any other pump, nutating mixer, or any other apparatus capable of agitating the cell culture medium below the insert is attached to the system. The entire assembly is then incubated. In some embodiments, one or more eukaryotic cells may be disposed between the coating and the gel, while in other embodiments a eukaryotic cell may be embedded in the gel of either one or both chambers or placed in the medium above in either one or both chambers. Other embodiments include separate tissue culture vessels for primary and secondary tissue sites.

More specifically, a method for forming the rMet model comprises 1) placing into a tissue culture insert with a porous membrane a eukaryotic cell and a biological matrix mimetic, wherein the mixture forms a gel, and wherein the eukaryotic cell is embedded in the gel; adding a second mixture onto a surface of the second mixture, the second mixture comprising a fluid from a vertebrate subject; 2) coating a portion of an interior surface of a tissue culture vessel with a first mixture, the first mixture comprising the extracellular matrix proteins specific for the basement membrane of the tissue; adding a second mixture onto the portion of the interior surface of the tissue culture vessel, the second mixture comprising a biological matrix mimetic, wherein the second mixture forms a gel; adding a third mixture onto a surface of the second mixture, the third mixture comprising a fluid from a vertebrate subject; 3) inserting (1) into (2) and incubating the assembly under conditions where the fluid in (2) is in motion, at a temperature of approximately 30-45° C., for example at approximately 37° C., and at 1-10% $CO_2$, for example at approximately 5% $CO_2$.

In an alternate embodiment, a method for the rMet model comprises 1) placing into a tissue culture insert with a porous membrane a biological matrix mimetic, wherein the mixture forms a gel, and wherein the eukaryotic cell is embedded in the gel; adding a second mixture onto a surface of the second mixture, the second mixture comprising a eukaryotic cell and fluid from a vertebrate subject; 2) coating a portion of an interior surface of a tissue culture vessel with a first mixture, the first mixture comprising the extracellular matrix proteins specific for the basement membrane of the tissue; adding a second mixture onto the portion of the interior surface of the tissue culture vessel, the second mixture comprising a biological matrix mimetic, wherein the second mixture forms a gel; adding a third mixture onto a surface of the second mixture, the third mixture comprising a fluid from a vertebrate subject; 3) inserting (1) into (2) and incubating the assembly under conditions where the fluid in (2) is in motion, at a temperature of approximately 30-45° C., for example at approximately 37° C., and at 1-10% $CO_2$, for example at approximately 5% $CO_2$.

In an alternate embodiment, a method for the rMet model comprises 1) placing into a tissue culture insert with a porous membrane a eukaryotic cell and a biological matrix mimetic, wherein the mixture forms a gel, and wherein the eukaryotic cell is embedded in the gel; adding a second mixture onto a surface of the second mixture, the second mixture comprising a fluid from a vertebrate subject; 2) coating a portion of an interior surface of a tissue culture vessel with a first mixture, the first mixture comprising the extracellular matrix proteins specific for the basement membrane of the tissue; adding a eukaryotic cells and a second mixture onto the portion of the interior surface of the tissue culture vessel, the second mixture comprising a biological matrix mimetic, wherein the second mixture forms a gel; adding a third mixture onto a surface of the second mixture, the third mixture comprising a fluid from a vertebrate subject; 3) inserting (1) into (2) and incubating the assembly under conditions where the fluid in (2) is in motion, at a temperature of approximately 30-45° C., for example at approximately 37° C., and at 1-10% $CO_2$, for example at approximately 5% $CO_2$.

In an alternate embodiment, a method for the rMet model comprises 1) placing into a tissue culture vessel a eukaryotic cell and a biological matrix mimetic, wherein the mixture forms a gel, and wherein the eukaryotic cell is embedded in the gel; adding a second mixture onto a surface of the second mixture, the second mixture comprising a fluid from a vertebrate subject; 2) coating a portion of an interior surface of a second tissue culture vessel with a first mixture, the first mixture comprising the extracellular matrix proteins specific for the basement membrane of the tissue; adding a eukaryotic cells and a second mixture onto the portion of the interior surface of the tissue culture vessel, the second mixture comprising a biological matrix mimetic, wherein the second mixture forms a gel; adding a third mixture onto a surface of the second mixture, the third mixture comprising a fluid from a vertebrate subject; 3) connecting tissue culture vessels (1) and (2) in such a way that a fluid from a vertebrate with cancer is moved through a biological matrix mimetic in each tissue culture vessel and incubating the assembly under conditions where the fluid in (2) is in motion, at a temperature of approximately 30-45° C., for example at approximately 37° C., and at 1-10% $CO_2$, for example at approximately 5% $CO_2$.

In an exemplary embodiment as described above, a method for preparing a culture apparatus for growth of eukaryotic cells in a multi-well tissue culture plate may comprise 1 well of a 24 well tissue culture plate (for other culture dishes adjust volumes accordingly).

Persons with ordinary skill in the art will readily understand that these exemplary methods may be modified to produce desired results. In some embodiments the matrix mixtures lack cells when initially added to the wells, while in other embodiments the matrix mixtures include cells. Labeled cells, normal cells, cancer cells and other cell types may be added to the matrix mixtures, alone or in combination. Additionally, growth media may be added to the some and/or all mixtures.

One skilled in the art will also realize that the optimal density of cells re-suspended and thereafter added to the individual mixtures is particular to each individual cell type. Therefore, the density listed in the steps above is to be varied through regular experimentation with a variety of densities. Embodiments contemplate a variety of densities of cells for inclusion in the rMet culture apparatuses and methods. Embodiments also contemplate the optional addition of additives including but not limited to anticancer compounds, antiviral compounds, antibacterial compounds, antifungal compounds, or media supplements, all of which are useful for encouraging the growth of cells of interest and discouraging the growth of cells, virus, or organisms not of interest.

As mentioned above, cell culture assemblies may also be horizontal. FIG. 2 illustrates an alternate set-up of the rMet culture where a microenvironment of a primary site that was shown in the cell culture insert in FIG. 1A is set-up in a separate tissue culture vessel from a microenvironment of a secondary site, which is set-up in a separate vessel, shown at the bottom of the assembly in FIG. 1A. The tubing connecting the two vessels represents the circulatory microenvironment depicted by the "secondary site medium" in FIG. 1A. The pump is set-up to move the fluid between vessels and is equivalent to the nutating mixer in FIG. 1A. Tumor-like cell population forms spheroids in the tissue culture vessel of a primary site, invasive fraction is formed by cells migrating through the matrix at a primary site, but remain attached to the membrane inside the tissue culture vessel. Metastatic fraction is formed by cells that travel from one tissue culture vessel to another.

An embodiment further provides an apparatus that supports in vitro expansion of primary tumor, invasive, and metastatic cell populations, providing access to cancer stem cells for further analysis. Apparatuses in accordance with embodiments provide a preclinical model for testing the impact of drugs and/or other therapies on a cellular compartment of rMet, a cancer cell, and/or a tumor. An embodiment provides an apparatus for the study of cytokine/chemokine and growth factor networks in normal and malignant tissues as well as cellular signaling in normal tissue homeostasis and in disease state tissue homeostasis. Additional embodiments provide apparatuses for high-throughput and/or high-content analysis of therapies with potential to target various cellular compartments, including but not limited to characterization of chemotherapeutic effect on individual cells, normal cells, cancer cells, and solid-phase tumors.

In some embodiments, one or more eukaryotic cells may be embedded within the biological matrix mimetic gel layer of the rMet model, while in other embodiments a eukaryotic cell is disposed into the fluid above a biological matrix mimetic. In an embodiment, a cell of a first type may be embedded within the middle gel layer while a cell of another type may be disposed between the bottom layer and the middle layer. rMet tissue culture assemblies may be further modified as described for rMet culture methods above.

Methods of Testing for Anticancer/Anti-Hyperproliferative Therapies

Embodiments disclose culture methods and apparatuses useful for the presently underexplored aspect of pre-clinical testing in which malignant cell expansion is observed within the context of the aggregate microenvironment. The rMet reconstruction of the tumor microenvironment provides an essential tool for evaluating the therapeutic potential of treatment strategies and new drugs on the entire malignant hierarchy.

In an exemplary embodiment, an rMet model for testing anticancer therapies reconstructs the microenvironments of the primary and secondary sites and allows a therapy to be applied to normal and/or cancer cells, which may then be examined to determine the effect of the therapy on the cell and potential toxicity and off target effects. In one embodiment is provided a method of identifying an anticancer (or anti-hyperproliferative (anti-HPP)) therapeutic comprising: a) adding a solution comprising a potential therapeutic to the cell culture assembly as described herein, wherein the second component of the cell culture assembly comprises a detectable amount of primary tumor, invasive, metastatic, cancer stem cells or HPP cells, b) detecting the amount of cancer cells present in the cell culture assembly before and after the addition of the potential therapeutic, and c) identifying a potential anticancer or anti-HPP therapeutic. In one embodiment, the cell culture assembly further comprises a system for detecting colonization of metastatic cells coupled to the assembly. In one embodiment, the assembly further comprises a digital microscope coupled to the assembly. In yet another embodiment, the cell culture assembly further comprises a flow cytometer coupled to the assembly.

In some embodiments, an apparatus is adapted for high-throughput screening/analysis by decreasing the size/volume of rMet tissue culture assemblies and/or using microtiter plates with 96 wells, 384 wells, 1536 wells, 3456 wells or any other number of wells. Cultures may be examined by an individual, by a computer, an automated machine, robotically, or by another method. rMet tissue culture assembly apparatuses may also be adapted for high-content screening and may include an automated image reader, a digital microscope/image reader, and/or a flow cytometer. Digital microscopes in accordance with various embodiments may be fluorescence microscopes, automated microscopes, confocal microscopes, widefield microscopes, etc. Additionally, embodiments of apparatuses for testing cancer therapies may include software for image analysis.

In some embodiments, a therapy is placed in the rMet assembly in any compartment, tubing, fluid, and/or matrix mimetic.

The embodiments provide a method for measuring the effect of a therapeutic on cells, including, but not limited to, cytotoxic, cytostatic, anti-proliferative, anti-migratory and/or some other effect, on any cell in an rMet assembly.

Methods of Identifying Efficacy of Anticancer Therapies

In an exemplary embodiment, an rMet apparatus for identifying the efficacy of anticancer therapies reconstructs the microenvironments of the primary and secondary sites and allows a therapy to be applied to normal and/or cancer cells, which may then be examined to determine the effect of the therapy on the cell. The embodiments provide a method for measuring the effect of a therapeutic on cells, including, but not limited to, cytotoxic, cytostatic, anti-proliferative and/or some other effect, on any cell in an rMet assembly. Cultures may be examined by an individual, by a computer, an automated machine, robotically, or by another method. rMet tissue culture assembly apparatuses may also be adapted for high-content screening and may include an automated image reader, a digital microscope/image reader, and/or a flow cytometer. Digital microscopes in accordance with various embodiments may be fluorescence microscopes, automated microscopes, confocal microscopes, widefield microscopes, etc. Additionally, embodiments of apparatuses for testing cancer therapies may include software for image analysis.

In one embodiment is provided a method of identifying the efficacy of an anticancer therapeutic on a patient's tumor comprising: a) adding a solution comprising a potential anticancer therapeutic to the first component of the cell culture assembly as described herein, wherein the second component of the cell culture assembly contains a detectable amount of metastatic cancer cells, b) detecting the amount of metastatic cancer cells present in the second component before and after the addition of the potential anticancer therapeutic, and c) identifying the efficacy of an anticancer therapeutic. In one embodiment, the cell culture assembly further comprises a system for detecting colonization of metastatic cells coupled to the assembly. In one embodiment, the assembly further comprises a digital microscope coupled to the assembly. In yet another embodiment, the cell culture assembly further comprises a flow cytometer coupled to the assembly.

In the embodiment the tumor cells from an individual vertebrate with cancer is cultured in rMet applying a therapy to the rMet assembly, measuring cytotoxic, cytostatic, anti-proliferative and/or some other effect. Individual therapies and/or combinations are applied to the rMet culture of a single vertebrate with cancer to identify therapies capable of eliminating cancer cells in any compartment of rMet. The process can be scaled for multiple individual vertebrates with cancer.

Methods of Predicting Metastatic Capacity of Tumors

In an exemplary embodiment, an rMet apparatus reconstructs the microenvironments of the primary and secondary sites for predicting the metastatic potential of individual tumor. The embodiments provide a method for measuring the migratory and dissemination capacity of tumor cells to identify individual tumors with a probability of forming metastasis. Cultures may be examined by an individual, by a computer, an automated machine, robotically, or by another method. rMet tissue culture assembly apparatuses may also be adapted for high-content screening and may include an automated image reader, a digital microscope/image reader, and/or a flow cytometer. Digital microscopes in accordance with various embodiments may be fluorescence microscopes, automated microscopes, confocal microscopes, widefield microscopes, etc. Additionally, embodiments of apparatuses for testing cancer therapies may include software for image analysis.

In one embodiment, is provided a method of predicting and/or identifying metastatic dissemination of a cancer in a patient comprising: a) adding a solution comprising cancer cells obtained from the patient to the first component of cell culture assembly as described herein, wherein the second component of the cell culture assembly comprises a detectable amount of cancer cells from the patient, and b) detecting the presence or absence of metastatic cancer cells in the second component of the cell culture assembly after a sufficient period of time. In one embodiment, the cell culture assembly further comprises a system for detecting colonization of metastatic cells coupled to the assembly. In one embodiment, the assembly further comprises a digital microscope coupled to the assembly. In yet another embodiment, the cell culture assembly further comprises a flow cytometer coupled to the assembly.

In the embodiment the tumor cells from a vertebrate with cancer is cultured in rMet assembly and detected metastatic cells capture the capacity of individual tumors to metastasize. The process can be scaled for multiple individual vertebrates with cancer.

The presently disclosed systems and methods are also useful for target screening and discovery and for evaluating toxicity and off target effects of a candidate therapeutic. For instance, the system can be coupled with microarrays, next generation sequencing, antibody arrays, mass spectrometry, and multiple other techniques to screen for therapeutics, combinations, or treatment schedules/regimens on non-malignant cells and tissues ex vivo utilizing the system described herein.

For instance, drug discovery can be based on the differential expression/production of genes, proteins, lipids, metabolites, and any other cellular or extracellular components between non-malignant, premalignant, non-metastatic, invasive, and metastatic cells, and cancer stem cells and any combination of the above. Off target effects of therapeutic agents can be evaluated based on the response of non-malignant cell populations incorporated into the rMet, such as stromal cells (fibroblasts, myoepithelial cells, adipocytes, osteoblasts, osteoclasts, etc.), blood cells (T cells, B cells, plasma cells, myeloid cells, etc.), epithelium, and any other non-cancerous tissues, to drug treatment.

In one embodiment, the presently disclosed systems can be used to evaluate response to a treatment by individual patients to single agents or combination treatments. For instance, tumor cells grown in rMet are exposed to the potential therapeutic modalities and the an optimal treatment can be chosen based on the cellular response to the treatment and off target toxicity.

EXAMPLES

Example 1

Exemplary rMet System for Use with a Mammary or Prostate Gland Primary Site and Bone Marrow Secondary Site The matrix mixtures in the rMet system where the primary site is a mammary or prostate gland and a secondary site is the bone marrow are set-up as follows. A 2 mg/ml stock solution of rat-tail collagen type I (BD Biosciences) was diluted in neutralization buffer (100 mM HEPES (Sigma) in 2× phosphate buffered saline (PBS)), pH 7.2-7.4. Reconstructed endosteum (rEnd), the extracellular matrix layer at the interface between the solid bone and the bone marrow, was a 63:5.3:1 v/v mixture of 1×PBS without $CaCl_2$ and $MgCl_2$ (Sigma), 1 mg/ml human plasma fibronectin (Millipore) and 2 mg/ml collagen I respectively. Reconstructed bone marrow (rBM) matrix was set-up as a 4:2.5:1:1 v/v mixture of Matrigel (BD biosciences), 1 mg/ml fibronectin, 2 mg/ml collagen I, and 2 mg/ml hyaluronic acid respectively.

The rMet system is as assembled as follows. Reconstructed bone marrow (rBM) is set-up in a 24-well tissue culture vessel adding 130 µl/well of rEnd matrix and incubating for 1 hr at 37° C., removing the excess liquid, adding rBM matrix at 75 µl/well and incubating for 1 hr at 37° C. The assembly of rBM is completed overlaying 1 ml of warm bone marrow stromal cell conditioned medium (BMCM) on top of solidified rBM matrix. BMCM was obtained by collecting conditioned medium from 3-day cultures of bone marrow stromal cells (growth medium: RPMI-1640 supplemented with $6.2 \times 10^{-4}$M $CaCl_2$, $1 \times 10^{-6}$M sodium succinate, $1 \times 10^{-6}$M hydrocortisone, 20% FBS, and 1% penicillin/streptomycin). Mammary/prostate microenvironment is set-up in the tissue culture insert with 8 µm pores (Corning) by mixing Matrigel (23 µl) with breast or prostate cancer cells at $2.5 \times 10^4$ cells/7 µl PBS/insert, pipetting the Matrigel/cell mixture into the cell culture insert, allowing the matrix/cell mixture to gel at 37° C. for 30 min, placing each insert into a well of a 24-well tissue culture vessel where the rBM matrix was previously set-up, and overlaying the cell/matrix mixture in the insert with 0.5 ml of warm growth medium (RPMI-1640 supplemented with 1% horse serum (Sigma) and 1% penicillin/streptomycin). The entire assembly is place on a nutating mixer to agitate the medium and placed in a 37° C., 5% $CO_2$ tissue culture incubator.

In order to visualize the polymerized matrix, cryo-scanning electron microscopy is used. For cryo-scanning electron microscopy, a small amount of Matrigel or rBM matrix was placed into a slit insert of the cryo holder, which was subsequently plunged into the liquid nitrogen slush. A vacuum was pulled and the sample was transferred to the Gatan Alto 2500 pre-chamber (cooled to −170° C.). After fracturing the sample with a cooled scalpel to produce a free-break surface, the sample was sublimated at −90° C. for 10 min followed by sputter coating with platinum for 120 sec. The sample was then transferred to the microscope cryostage (−130° C.) for imaging.

Based on the information in Table IA and IB, this system may be adapted for a number of different primary sites and secondary sites.

Example 2

Recolonization of Various Metastatic Cancer Cells in rMet System

Figure 3A:
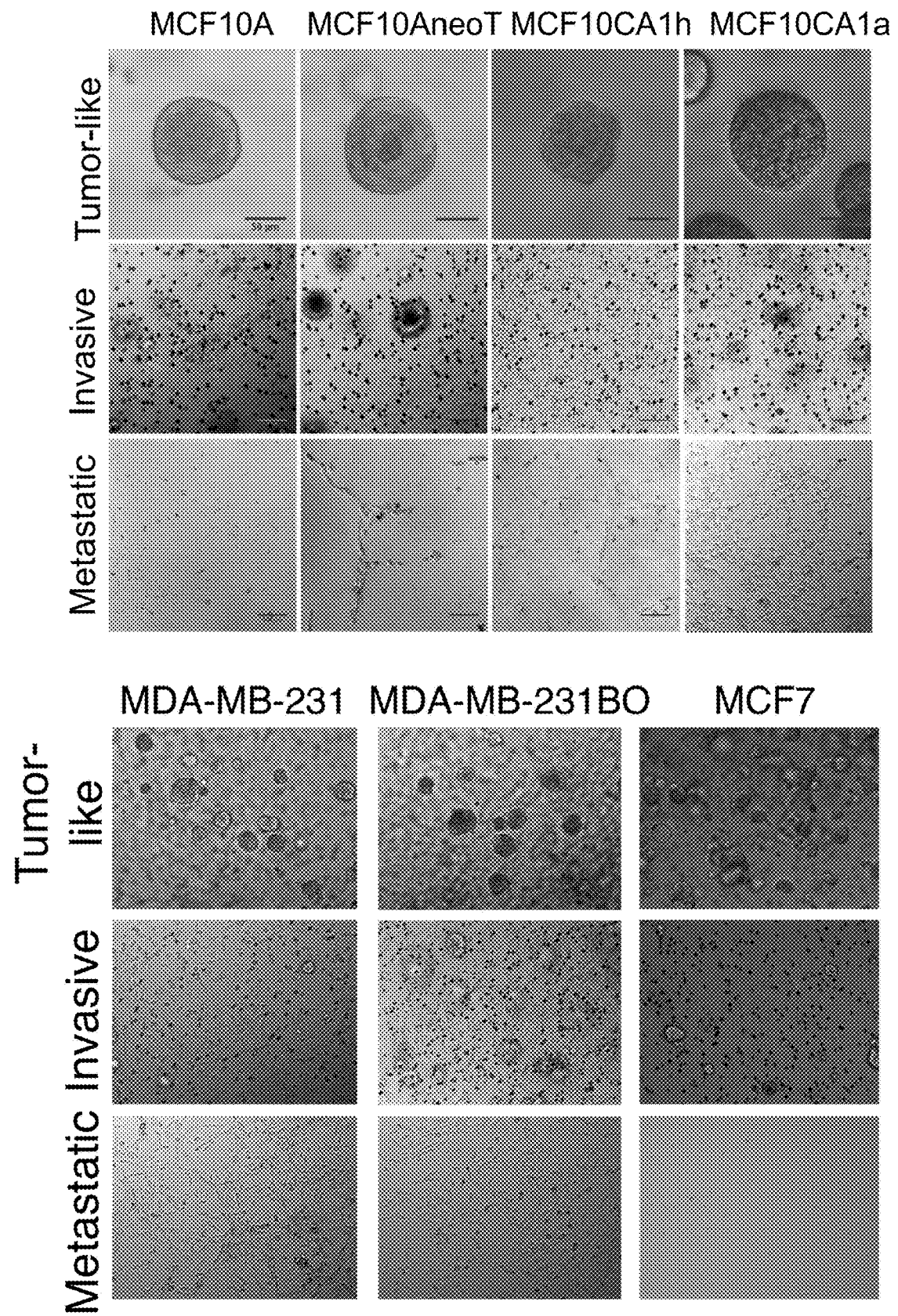
Figure 3D:
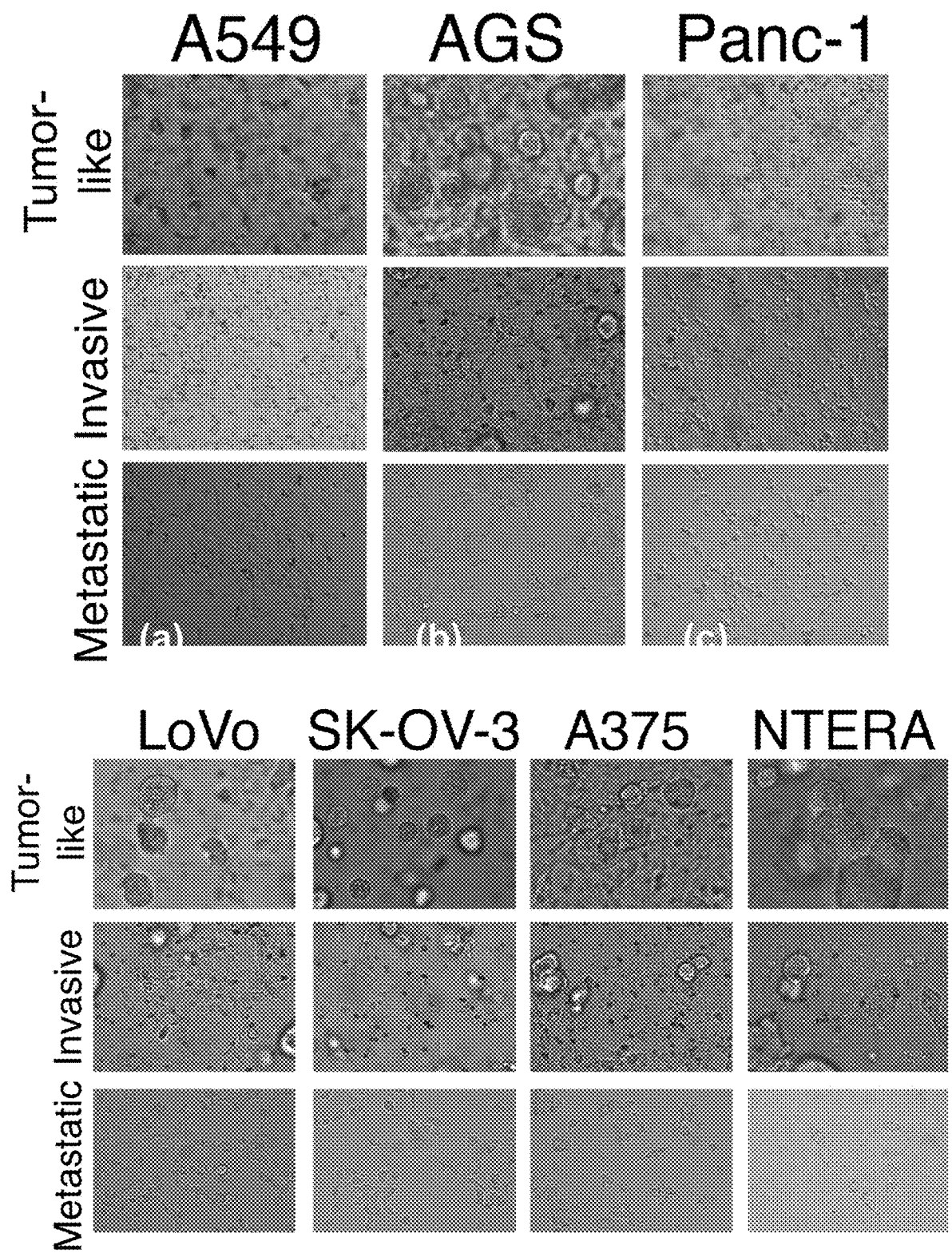
Figure 4:
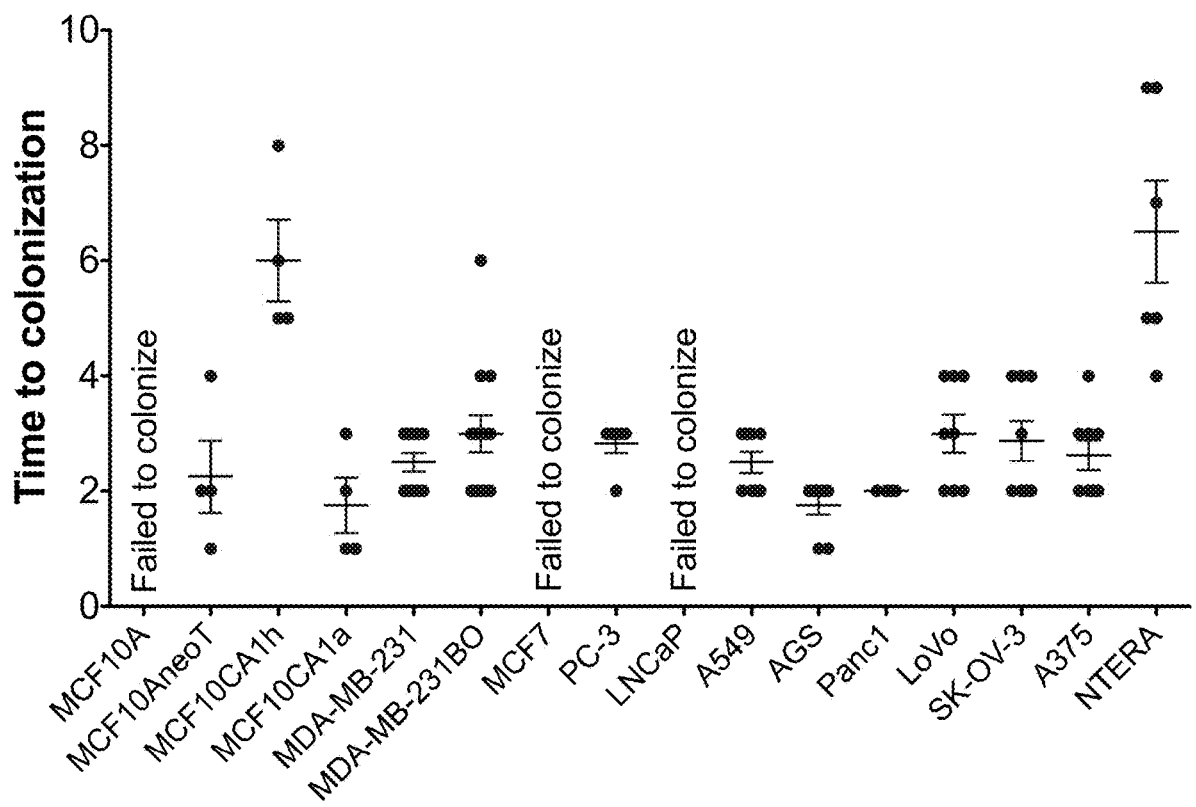
FIG. 4 illustrates the timing of colonization of the "metastatic site" based on the tumor type.

In the embodiments illustrated in FIGS. 3 and 4, various cell lines were tested in the rMet system in a manner similar to as described in Example 1. The following cell lines were tested: breast cancer (MCF10A, MCF10AneoT, MCF10CA1h, MCF10CA1a, MDA-MB-231, MDA-MB-231BO, MCF7), prostate cancer (PC-3 and LNCap), lung cancer (A549), stomach cancer (AGS), pancreatic cancer (Panc-1), colon cancer (LoVo), ovarian cancer (SK-OV-3), melanoma (A375), testicular cancer (NTERA-2) cell lines were grown in rMet cultures. Cell lines were obtained from ATCC and from Barbara Ann Karmanos Cancer Institute. Breast cancer cells isolated from patients with invasive and metastatic cancer were also tested in the rMet model. Further details on preparation of the assembly, including the various matrices employed, are provided below.

Preparation of Polymerized Collagen I Gel

1) Prepared neutralization buffer: 100 mM HEPES in 2×PBS. The pH of this solution was about 7.0.
2) A 2 mg/ml collagen I solution was prepared by diluting 10.21 mg/ml rat tail collagen I in the neutralization buffer. The solution was vortexed at low speed or mixed well using pipette.
3) The solution prepared in step 2 was added to the plate well and incubated for at least 1 hour at 37° C. to allow it to polymerize well and form a gel. The volume to be added was determined according to desired thickness of the gel.

Preparation of Reconstructed Endosteum (rEnd)

1) For making 5 ml rEnd, 384.6 µl of fibronectin (1 mg/ml stock), 72.3 µl of collagen I (2 mg/ml stock), and 4.543 ml 1×PBS was mixed and then kept on ice.

Preparation of Reconstructed Bone Marrow Matrix (rBM)

1) For making rBM 104 µl of Matrigel, 68 µl of fibronectin (1 mg/ml stock), 28 µl of collagen I (2 mg/ml stock), and 28 µl hyaluronic acid (2 mg/ml) was mixed and then kept on ice.

Preparation of Bone Marrow Growth Medium (BMGM)

1) For making BMGM 500 µl calcium chloride (0.62M stock), 500 µl of sodium succinate ($1 \times 10^{-3}$M stock), 500 µl of hydrocortisone ($1 \times 10^{-3}$M stock), and 1% penicillin/streptomycin, was added to 10% FBS to 394 ml of RPMI-1640.

Mammary Epithelial Growth Medium (MEGM)

1) For making MEGM 1% penicillin/streptomycin, 1% horse serum was added to 490 ml of RPMI-1640.

Set-Up of the Reconstructed Metastasis (rMet Model)

1) Matrigel was thawed overnight at 4° C.
2) rEnd, rBM, MEGM and BMGM were prepared as described above.
3) 130 µl rEnd was added per well of a 24 well plate.
4) This was incubated for 1 hour at 37° C.
5) After 1 hour of incubation with rEnd, the solution was removed from wells and 75 µl rBM was added to the center of each well each, and the plate was incubated for 1 hr at 37° C.
6) Twenty five thousand cells in 7 µl PBS were mixed with 23 µl Matrigel for each well of the 24-well plate.
7) The mixture from step 6 was gently added to the membrane of the insert and was spread evenly.
8) The cell/Matrigel mixture was incubated for 30 min at 37° C.
9) Once the matrices in the tissue culture plate and the insert have solidified, each insert was placed into the well of 24 well plate with the previously set-up matrix.
10) 1 ml of BMGM was added to each well of the tissue culture plate.
11) Four hundred microliters of MEGM were added into the insert.
12) The entire assembly was placed on a nutating mixer and placed into an incubator at 37° C. and 5% carbon dioxide.

For brightfield microscopy cells were cultured in the rMet model for 12-14 days and brightfield images of top, invasive and metastatic fractions were taken using Zeiss AxioObserver inverted microscope equipped with Axiovision software 4.7.3 (Zeiss). Zeiss Axiovert 40C inverted microscope was used to observe cell migration through the rMet.

Panels presented in FIG. 3 illustrate that human breast cancer cell lines (FIG. 3A), primary human breast cancer cells (FIG. 3B), prostate cancer (FIG. 3C), lung cancer (FIG. 3D(a)), stomach cancer (FIG. 3D(b)), pancreatic cancer (FIG. 3D(c)), colon cancer (FIG. 3D(d)), ovarian cancer (FIG. 3D(e)), melanoma (FIG. 3D(f)), and testicular cancer cell lines (FIG. 3D(g)) were cultured for 14 days in the rMet model and imaged. All tumor types gave rise to a primary tumor-like fraction, an invasive fraction consisting of cells growing on the membrane of cell culture insert (dark spots: pores in the membrane), and a metastatic fraction.

FIG. 4 illustrates that the propensity of the cells to metastasize in the rMet model closely matches the propensity of the cells to metastasize in vivo. Highly metastatic cells, for example, MCF10CA1a, MDA-MB-231, MDA-MB-231BO, PC-3, A549, and AGS, robustly formed a metastatic fraction in rMet occupying >90% of a tissue culture vessel after 14 days in rMet. Moderately metastatic cells, for example, Panc-1, LoVo, and SK-OV-3, formed a metastatic fraction occupying 50-75% of a tissue culture vessel. Weakly metastatic cells, for example, MCF10AneoT, MCF10CA1h, A375, and NTERA-2, formed a sparse metastatic fraction, and non-metastatic cells, for example, MCF10A, MCF7, and LNCaP did not form a metastatic layer in rMet.

Table II provides the migratory characteristics of various cells lines used in the systems described herein.

TABLE II

Metastatic and rMet migratory characteristics of various cancer lines

| Cell lines | Organ | Metastatic (rMet) | Metastatic (in vivo) |
|---|---|---|---|
| MCF10A | Breast | − | No**** |
| MCF10AneoT | Breast | ++ | Weakly*** |
| MCF10CA1h | Breast | ++ | Weakly*** |
| MCF10CA1a | Breast | +++ | Strongly* |
| MDA-MB-231 | Breast | +++ | Strongly* |
| MDA-MB-231BO | Breast | +++ | Strongly* |
| MCF7 | Breast | − | No**** |
| PC-3 | Prostate | +++ | Strongly* |
| LNCaP | Prostate | − | No**** |
| A549 | Lung | +++ | Strongly* |
| AGS | Stomach | +++ | Strongly* |
| Panc-1 | Pancreas | ++ | Moderately** |
| LoVo | Colon | ++ | Moderately** |
| SK-OV-3 | Ovarian | ++ | Moderately** |
| A375 | Melanoma | ++ | Weakly*** |
| NTERA-2 | Testicular | + | Weakly*** |

Figure 5:
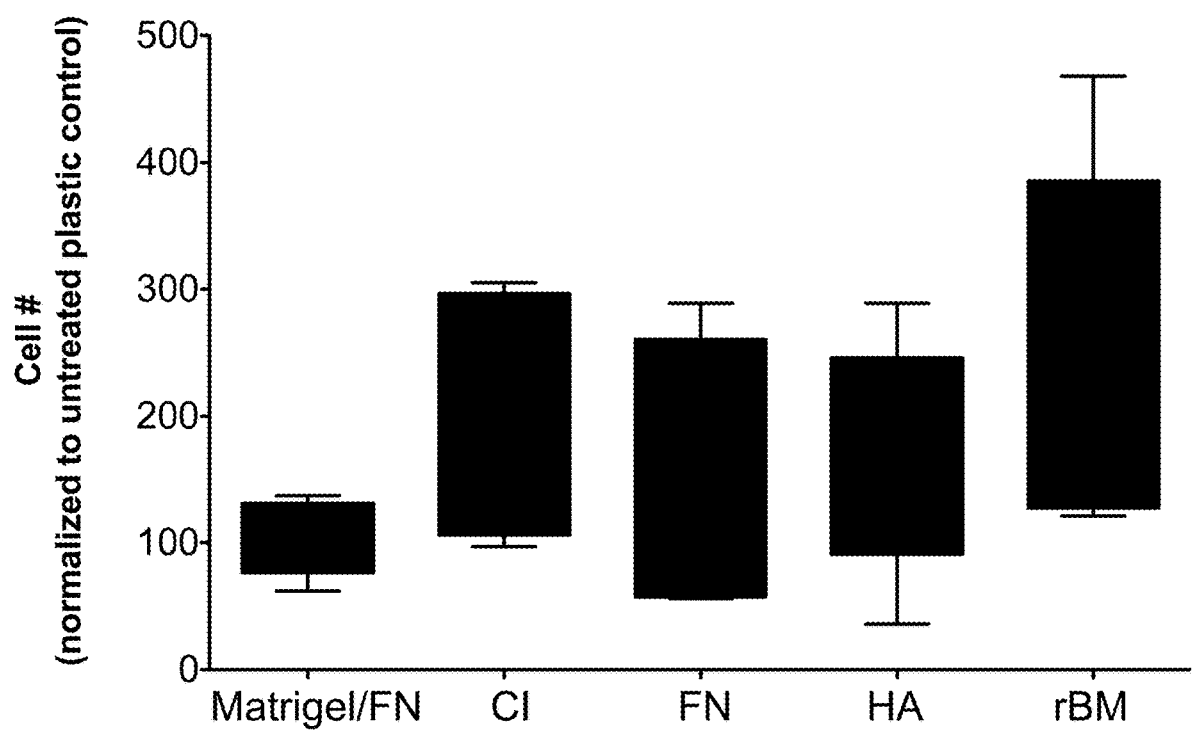
FIG. 5 illustrates the propensity of cells to establish metastatic colonization based on the matrix substratum at the "metastatic site" of the rMet.

*Strongly metastatic: >85% of animals develop metastatic lesions
**Moderately metastatic: 50-85% of animals develop metastatic lesions
***Weakly metastatic: <50% of animals develop metastatic lesions
****Non-metastatic: no detectable metastatic lesions FIG. 5 illustrates the effects of matrix components on maintaining the metastatic capacity of cells in rMet. The bottom chamber of the rMet culture (the tissue culture vessel) was set-up with various matrix components or their mixtures (Matrigel/fibronectin, collagen I (CI), fibronectin (FN), hyaluronic acid (HA), or rBM (mixture of Matrigel, collagen I, fibronectin, hyaluronic acid) and the formation of a metastatic fraction was visualized after 14 days in rMet culture. rBM was capable of sustaining the highest number of metastatic cells, while Matrigel/fibronectin mixture or individual components could not sustain the formation of a metastatic fraction at comparable levels (p-value=0.0056).

Example 3

Viability of Cells in rMet System

In the embodiments illustrated in FIG. 6 the rMet cell culture was performed, and subsequently, cell viability of each fraction was measured. The cell assembly was produced according to Example 1. The following cell lines were tested: breast cancer (MDA-MB-231, MDA-MB-231BO, MCF7), prostate cancer (PC-3 and LNCap), lung cancer (A549), stomach cancer (AGS), pancreatic cancer (Panc-1), colon cancer (LoVo), ovarian cancer (SK-OV-3), melanoma (A375), testicular cancer (NTERA-2).

To measure cell viability after 12-14 days of culture in the rMet model, tumor-like, invasive, and metastatic fractions were stained using the LIVE/DEAD viability/cytotoxicity kit (Life Technologies), per manufacturer's instructions. Briefly, cells were incubated with 1 µM of calcein AM and ethidium homodimer-1 for 30 min at 37° C. Calcein and ethidium-generated fluorescence was imaged within 1 hr of staining on a Zeiss AxioObserver microscope using 493 nm and 528 nm filter sets respectively. Images were edited for brightness, contrast or size and scale bar was added using ImageJ software (version 1.46r; NIH).

Figure 6:
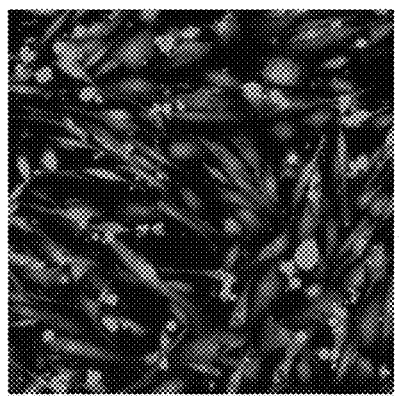
FIG. 6 demonstrates that metastatic cells in the rMet model remain viable.
Figure 6:
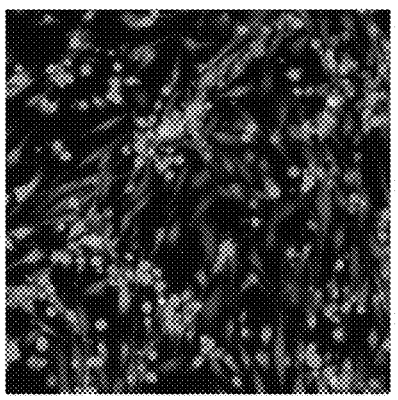
Figure 6:
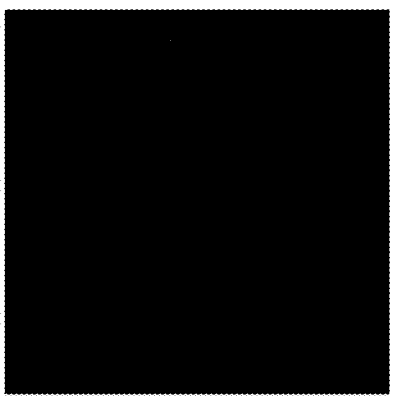
Figure 6:
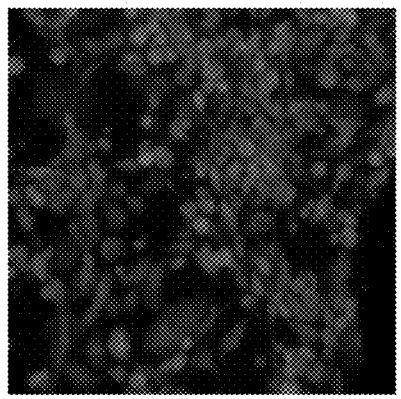
Figure 6:
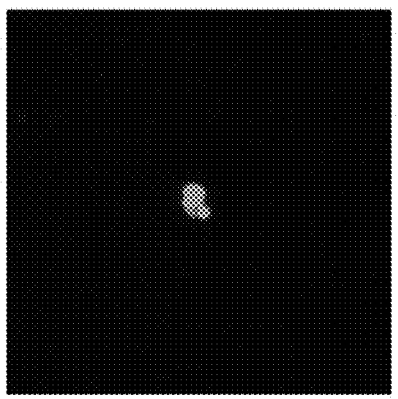
Figure 6:
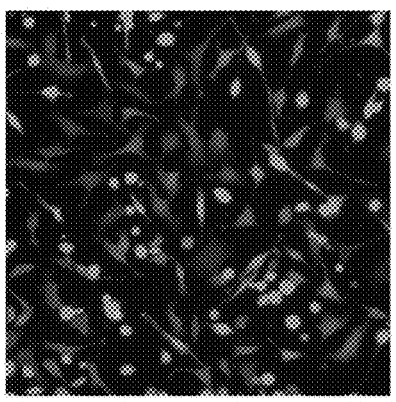
Figure 6:
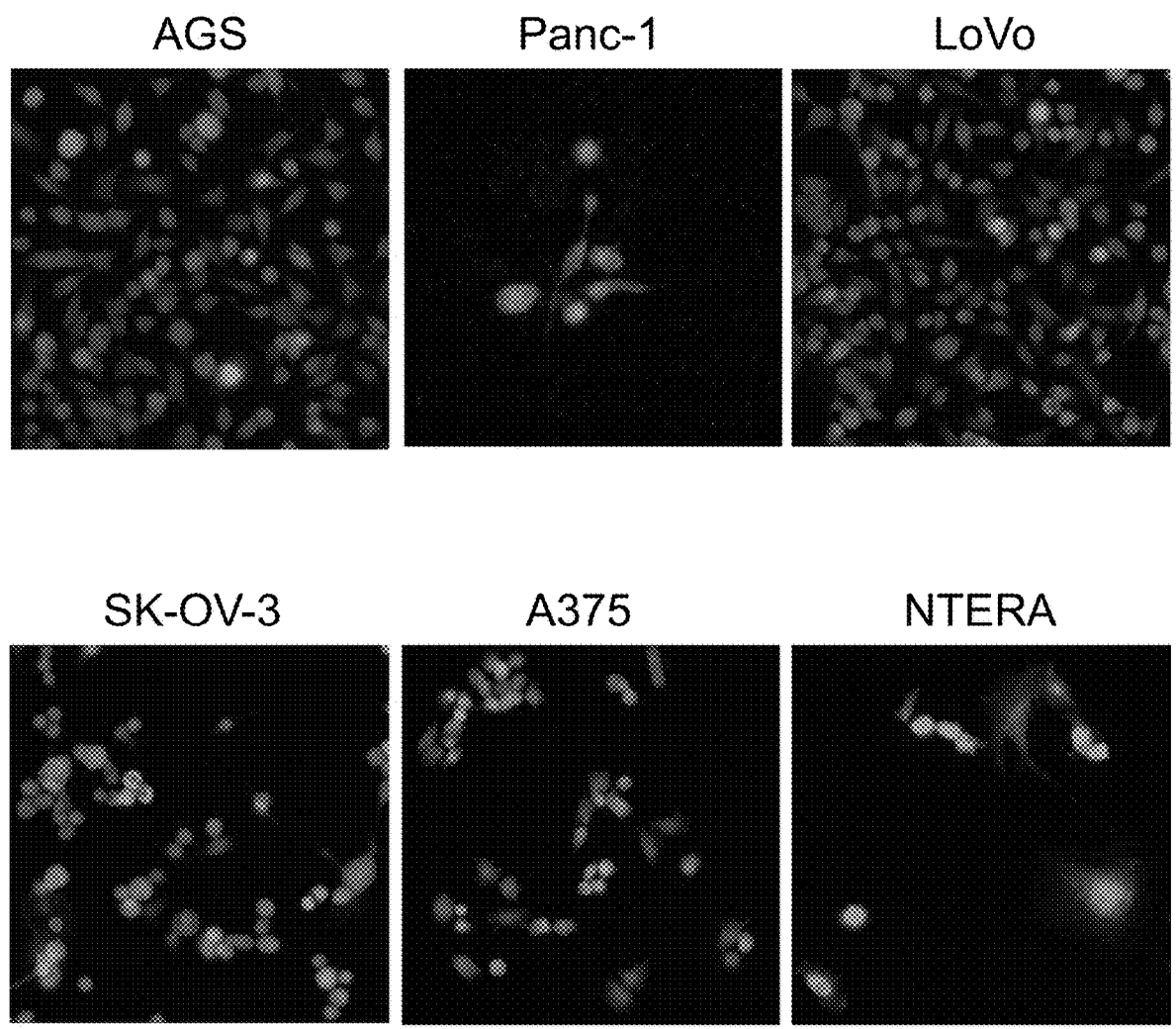

FIG. 6 illustrates that after culturing each cell line for 14 days in the rMet model the majority of metastatic cells (>95%) are viable in rMet (green: calcein AM positive, live cells; red: ethidium homodimer-1 positive, dead cells).

Example 4

Comparison of rMet System with Xenograft Model

In the embodiments illustrated in FIG. 7 a xenograft model was set-up to validate the metastatic capacity of a metastatic fraction from the rMet.

To assess the metastatic potential of cells from the rMet model, tumor-like and metastatic fractions were isolated from the 14-day rMet cultures using Cell Recovery Solution (CRS) (BD biosciences) according to the manufacturer's instructions with the following modifications. Media was removed from the top and bottom chambers of the rMet system, 565 μl and 1585 μl of ice cold CRS was added to the remaining matrix layer in the cell culture insert and the plate respectively. The CRS/cell/matrix mixture was transferred to a microcentrifuge tube and incubated for 1 hr on ice. Subsequently, cells were centrifuged at 1800 rpm for 10 min to remove CRS and washed 2× with PBS. The cell pellet was resuspended in 1×PBS for injection. One hundred microliters of primary tumor-like or metastatic cells were injected into the left ventricle of NOD.Cg-Prkdcscid Il2rgtm1Wjl/SzJ (NSG) mice (Jackson Labs), using a 27½-gauge needle. Mice were anesthetized using isoflurane (2.0-2.5% in 3.0 L/min $O_2$; VetEquip table-top vaporizer). All animal experiments were performed after approval from the Animal Care and Use Committee. Animals were sacrificed using $CO_2$ asphyxiation/cervical dislocation when they presented with weakness, loss of mobility, weight loss, or appearance of palpable tumors >1 $cm^3$. During necropsy, images of organ involvement and metastatic lesions were acquired using Canon Powershot A650 IS digital camera.

Figure 7A:
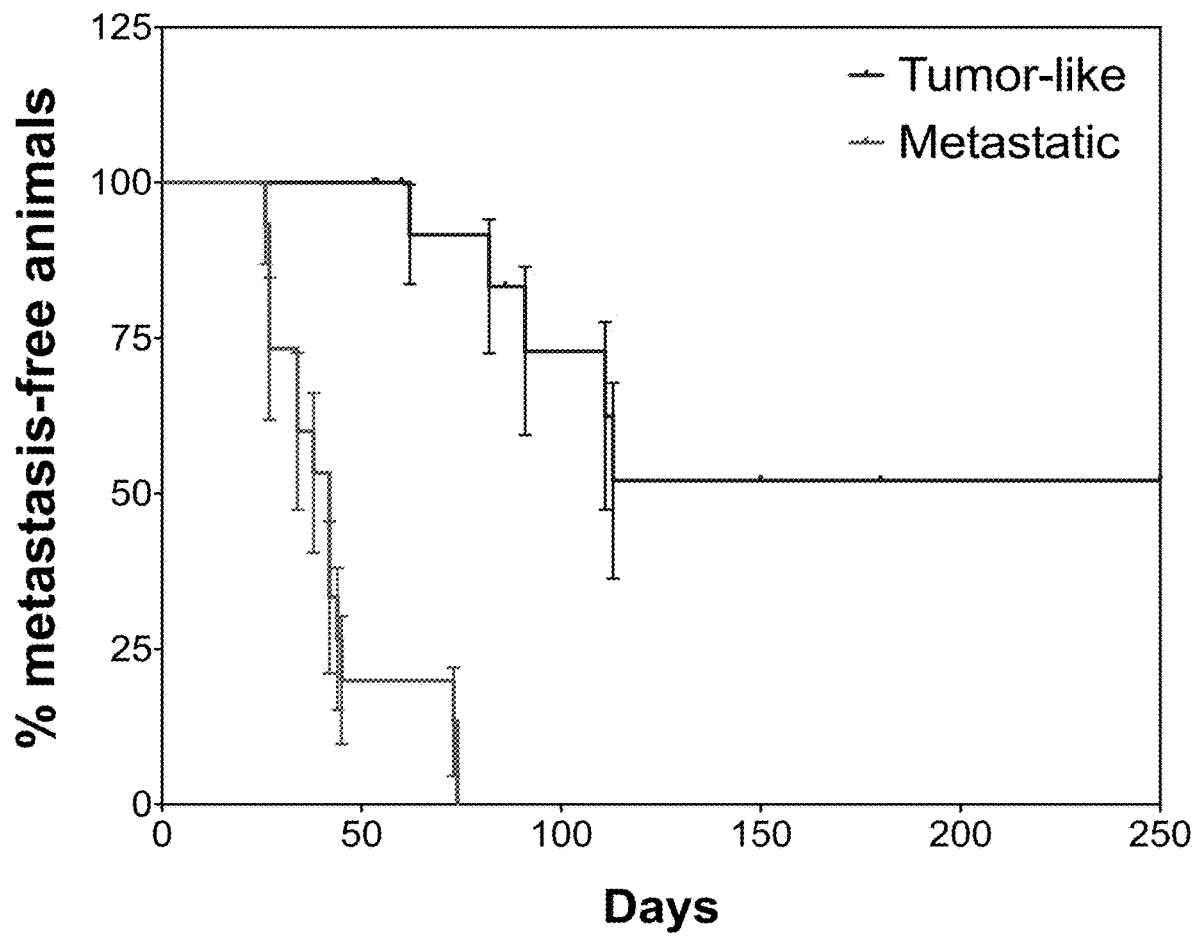
FIGS. 7A-B illustrate the metastatic capacity of cells isolated from the rMet.

FIG. 7A illustrates that compared to the primary tumor-like population, metastatic population derived from the rMet produces metastatic lesions at high frequency and with 100% sensitivity (i.e. all animals injected with the metastatic fraction develop distant site metastases).

Figure 7B:
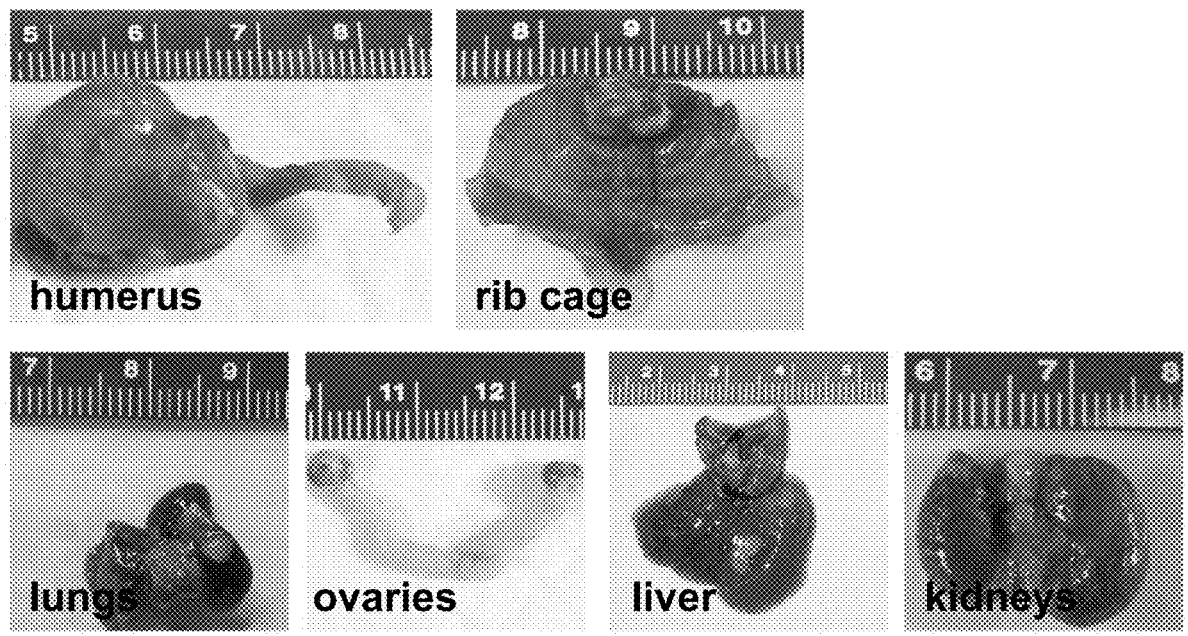
Figure 8:
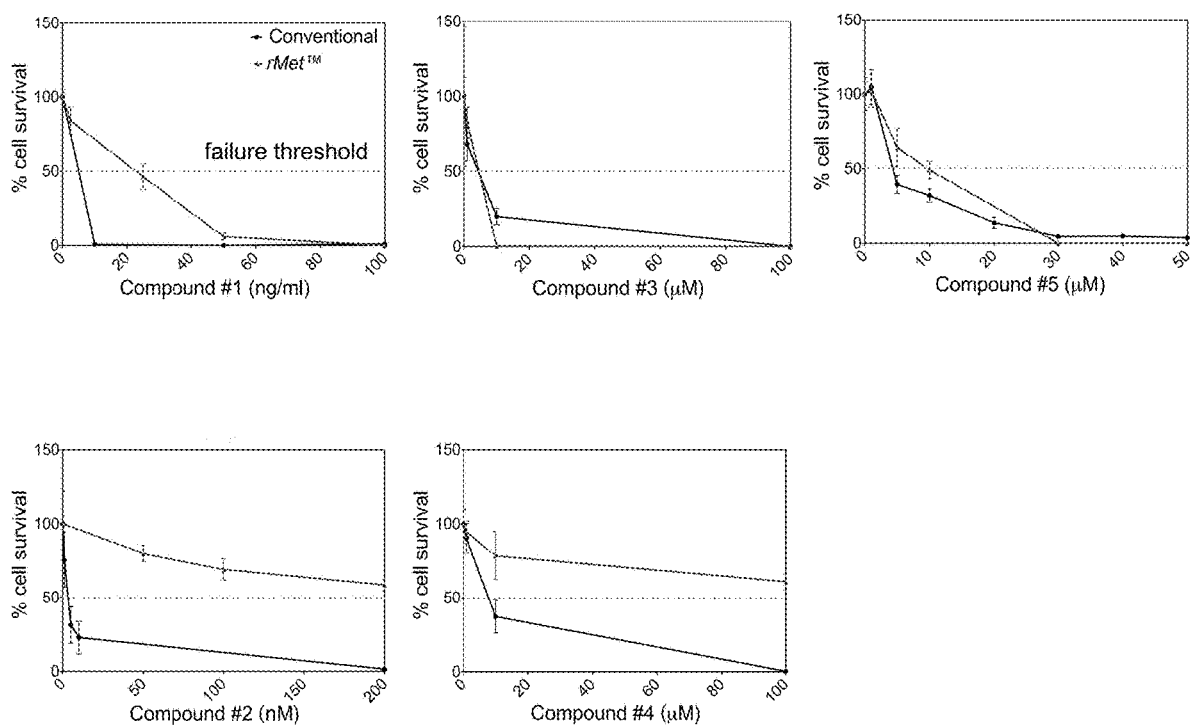
FIG. 8 demonstrates the advantages of using the rMet platform for efficacy testing as compared to the conventional culture methods.

FIG. 7B provides examples of metastatic lesions at secondary sites such as bone, lungs, ovaries, liver, and kidney.

Example 5

Tumor cells harvested from xenografts were assessed for the presence of human leukocyte antigen (HLA) by flow cytometry.

Tumor fragments were chopped into small pieces and incubated in 0.5-1 mg/ml collagenase (Sigma) or liberase (Roche) for 30 min at 37° C., with shaking at 700 rpm. Growth medium was added to inactivate the enzymes and dissociated cells were passed through a 40 μm cell strainer (BD), centrifuged at 3000 rpm for 10 min, and washed once with 1×PBS and centrifuged again. Cells were flushed from the BM of femurs and tibias with 30-40 ml of 1×PBS using a 10 ml syringe with a 27½-gauge needle. Flushed cells were pipetted up/down to break any aggregates, passed through a 40 μm cell strainer, and centrifuged at 3000 rpm for 10 min. Cell pellets were resuspended in distilled water for 1 min to lyse red blood cells. Subsequently, several volumes of 1×PBS was added and cells were centrifuged at 3000 rpm for 10 min. Dissociated cells were fixed with 10% neutral buffered formalin (NBF) for 15 min at room temperature, centrifuged at 3000 rpm for 10 min, washed once with PBS, and stored at 4° C. in PBS. Non-specific binding was blocked using the rat anti-mouse CD16/32 Fc Block reagent (BD Pharmingen) and M.O.M kit (Vector laboratories) per manufacturer's instructions. Cells were incubated with mouse anti-HLA-A-C-PE-Cy5 or mouse IgG1κ-PE-Cy5 isotype control (BD Pharmingen) for 1 hr (1:50 dilution) and analyzed on a Beckman Coulter FC500 flow cytometer. Data analysis was done using FlowJo software (version 10.0.6).

Cells isolated from the metastatic lesions were positive for the human leukocyte antigen (HLA) demonstrating each lesion was derived from the injected human cells. Based on a paired t-test analysis, there was a statistically significant increase in the HLA positive cells in the metastatic lesions of mice injected with the metastatic fraction (p-value=0.021), while there was no increase in HLA-positive staining above the levels of isotype control in mice injected with the tumor-like fraction of the rMet (p-value>0.05).

Example 6

In situ zymography was used to detect matrix metalloproteinase (MMP) activity. Cells were cultured in the rMet model as described above, with DQ-FITC collagen I or IV (Life Technologies) incorporated into the Matrigel and rBM matrices at 50 μg/ml per manufacturer's instructions. MMP secretion was monitored over 14 days with fluorescence microscopy using a Zeiss AxioObserver inverted microscope. At each time point images were acquired at the same exposure time at an excitation wavelength of 495 nm. Images were edited for brightness, contrast and size using ImageJ (version 1.46r; NIH) or Adobe Photoshop CS6 extended (version 13.0).

Example 7

To demonstrate the preclinical capabilities of rMet, conventional and rMet preclinical models were utilized to evaluate the efficacy of five therapeutics. Compounds #1, 3, and 5 exhibited minimal resistance when evaluated in rMet system and demonstrated in vivo and clinical activity. Compound #2 failed phase II clinical trials and compound #4 was abandoned; both demonstrated poor activity in rMet (rMet curve remains above the failure threshold). Accordingly, this example demonstrates the high correlation of testing results from the rMet system with clinical trial results. Such a correlation, therefore, underscores the value of the rMet system in predicting clinical performance of a candidate cancer therapeutic.

For statistical analysis at least three independent biological replicas were performed for each experiment. Time taken by metastatic or non-metastatic cells to initiate colonization in the rBM was compared using a chi-square test. Statistical significance for survival time and presence of HLA positive cells in the BM, was determined using a log-rank test and paired t-test respectively. Data were represented as mean±SD. All analyses were done using GraphPad Prism software (version 5.0a for Mac; San Diego, Calif.; www.graphpad.com) and p<0.05 values were considered significant.

Some embodiments may comprise only an rMet tissue culture assembly and an incubator, while other embodiments may further comprise an automated image reader, a digital microscope, and/or a flow cytometer. In some embodiments of an rMet tissue culture apparatus, an automated image reader may be coupled to a digital microscope and/or a flow cytometer, and/or a digital microscope may be coupled to a flow cytometer. In some embodiments, any or all of these components may be coupled to and/or controlled through a computer and/or a user interface. In some embodiments adapted for high-throughput and/or high-content screening, control of some or all components may be automated.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

The invention claimed is:

1. A cancer cell culture assembly comprising:
   (i) a first component comprising a primary site growth medium derived from a vertebrate overlaid on a primary site growth matrix comprising tumor cells,
   (ii) a second component comprising a secondary site matrix mimetic, and
   (iii) a dynamic fluid component comprising a secondary site growth medium,
   wherein the dynamic fluid component is in fluid contact with the primary site growth matrix and the secondary site matrix mimetic, allowing cells to migrate from the primary site growth matrix through the dynamic fluid component to the secondary site matrix mimetic,
   wherein the secondary site growth medium has a higher serum concentration than the primary site growth medium,
   wherein the first component, or the second component, or both, further comprise a test anticancer or anti-hyperproliferative (anti-HPP) therapeutic.

2. The cancer cell culture assembly of claim 1, wherein the secondary site growth medium contains at least 8% serum or serum substitute.

3. The cancer cell culture assembly of claim 1, wherein the secondary site growth medium contains at least 15% serum or serum substitute.

4. The cancer cell culture assembly of claim 2, wherein the secondary site growth medium contains less than 5% serum or serum substitute.

5. The cancer cell culture assembly of claim 2, wherein the secondary site growth medium has serum concentration that is at least twice of that in the primary site growth medium.

6. The cancer cell culture assembly of claim 1, wherein the first component and the second component are contained within separate tissue culture vessels.

7. The cancer cell culture assembly of claim 1, wherein the first component is at least partially contained within an insert vessel.

8. The cancer cell culture assembly of claim 1, further comprising a pump or an agitation apparatus coupled to the dynamic fluid component.

9. The cancer cell culture assembly of claim 1, wherein the primary site growth medium derived from a vertebrate in the first component comprises a fluid obtained from a healthy vertebrate.

10. The cancer cell culture assembly of claim 1, wherein the primary site growth medium derived from a vertebrate in the first component comprises a fluid obtained from a vertebrate with cancer.

11. The cancer cell culture assembly of claim 1, wherein the dynamic fluid component comprises a fluid obtained from a vertebrate with cancer.

12. The cancer cell culture assembly of claim 1, wherein the dynamic fluid component comprises a fluid obtained from a culture of bone marrow stromal cells.

13. The cancer cell culture assembly of claim 1, wherein the secondary site matrix mimetic comprises organ-specific matrix.

14. The cancer cell culture assembly of claim 13, wherein the organ-specific matrix simulates the adrenal gland, bone marrow, brain, liver, lung tissue, lymph node, ovary, peritoneum, skin, spleen, connective tissue, bone, vascular structure, or articular joint.

15. The cancer cell culture assembly of claim 1, wherein the secondary site matrix mimetic comprises collagens 1-14 or fragments thereof, elastin, laminin, fibronectin, hyaluronic acid or related hyaluronans, lecticans, glycosaminoglycans, chondroitins, dermatans, or related extracellular matrix or glycocalyx components or combinations thereof.

16. The cancer cell culture assembly of claim 1, wherein the first component mimics a solid tumor of the bladder, bone, bone marrow, brain, breast, cervix, colon, endometrium, esophagus, kidney, liver, lung, skin, ovary, pancreas, prostate, stomach, testicle, thyroid, or uterus, endothelial cells, smooth muscle cells, pericytes, scars, fibrotic tissue, surgical adhesion tissue or hyperproliferative bone lesions.

17. The cancer cell culture assembly of claim 1, wherein the first component comprises collagen I, collagen II, collagen III, collagen IV, collagen-V, elastin, laminin, fibronectin, hyaluronic acid, lecticans, Matrigel® or combinations thereof.

18. The cancer cell culture assembly of claim 1, wherein the system is maintained at a temperature of from about 30° C. to about 45° C.

19. The cancer cell culture assembly of claim 1, further comprising a microscope coupled to the assembly for detecting colonization of metastatic cells.

20. The cancer cell culture assembly of claim 1, wherein the composition of the matrix in the primary site growth matrix is different from the composition of the matrix in the secondary site matrix mimetic.

* * * * *